United States Patent
Rozwadowski et al.

(10) Patent No.: US 10,179,211 B2
(45) Date of Patent: Jan. 15, 2019

(54) SAFETY NEEDLE DEVICE

(71) Applicant: HTL-STREFA SPOLKA AKCYJNA, Ozorkow (PL)

(72) Inventors: Marcin Rozwadowski, Warsaw (PL); Vincent Leskowich, Karpathos (GR)

(73) Assignee: HTL-STREFA SPOLKA AKCYJNA, Ozorkow (PL)

( * ) Notice: Subject to any disclaimer, the term of this patent is extended or adjusted under 35 U.S.C. 154(b) by 309 days.

(21) Appl. No.: 15/024,331

(22) PCT Filed: Oct. 28, 2013

(86) PCT No.: PCT/PL2013/050024
§ 371 (c)(1),
(2) Date: Mar. 24, 2016

(87) PCT Pub. No.: WO2015/047114
PCT Pub. Date: Apr. 2, 2015

(65) Prior Publication Data
US 2016/0228654 A1    Aug. 11, 2016

(30) Foreign Application Priority Data
Sep. 30, 2013   (PL) .................................... 405486

(51) Int. Cl.
*A61M 5/00* (2006.01)
*A61M 5/32* (2006.01)
(Continued)

(52) U.S. Cl.
CPC ..... *A61M 5/3245* (2013.01); *A61B 5/150183* (2013.01); *A61B 5/150641* (2013.01);
(Continued)

(58) Field of Classification Search
CPC .......... A61M 5/326; A61M 2005/3247; A61M 2005/3267; A61M 5/3202;
(Continued)

(56) References Cited

U.S. PATENT DOCUMENTS 5,092,851 A * 3/1992 Ragner ................. A61M 5/002
604/192
5,944,700 A   8/1999 Nguyen et al.
(Continued)

FOREIGN PATENT DOCUMENTS

DE   102006022081 B3   5/2006
EP      0749758 B1     8/2002
(Continued)

OTHER PUBLICATIONS

Search Report by the Polish Patent Office dated Feb. 25, 2014, issued in parent application No. 405486.
(Continued)

*Primary Examiner* — Kami A Bosworth
*Assistant Examiner* — William Carpenter
(74) *Attorney, Agent, or Firm* — Wentsler LLC

(57) ABSTRACT

The invention relates to a safety needle device, for a medical instrument, to insert a needle into a patient's body to a determined insertion depth. The safety needle device, in two variants with a fixed insertion depth and with an insertion depth adjustment, comprises a hub, a needle, a protecting shield, longitudinal resilient means, transverse resilient means, a housing, and is provided with different technical means configured to cooperate with each other in order to perform different functions of the device. The safety needle device enables to control a state of use of the device, wherein the device is a disposable one and it ensures its user a protection against an accidental or intentional prick of the
(Continued)

needle before and after the due use of the device for the purpose for which it is intended.

30 Claims, 14 Drawing Sheets

(51) Int. Cl.
*A61M 5/46* (2006.01)
*A61B 5/15* (2006.01)
*A61B 10/02* (2006.01)

(52) U.S. Cl.
CPC ......... *A61B 10/0233* (2013.01); *A61M 5/326* (2013.01); *A61M 5/46* (2013.01); *A61M 2005/3246* (2013.01); *A61M 2005/3247* (2013.01); *A61M 2005/3267* (2013.01)

(58) Field of Classification Search
CPC .......... A61M 2005/325; A61M 5/3213; A61M 5/3272; A61M 5/3257; A61M 5/347; A61M 5/3271; A61M 2005/3254; A61M 2005/3246; A61M 5/3245; A61M 5/46
USPC ....... 604/110, 163, 171, 192, 195, 198, 241, 604/263, 272
See application file for complete search history.

(56) References Cited

U.S. PATENT DOCUMENTS

| | | | | |
|---|---|---|---|---|
| 6,096,005 | A | * | 8/2000 | Botich ................ A61M 5/3129 604/110 |
| 6,629,959 | B2 | | 10/2003 | Kuracina et al. |
| 7,101,351 | B2 | | 9/2006 | Crawford et al. |
| 7,815,611 | B2 | | 10/2010 | Giambattista et al. |
| 8,062,265 | B2 | | 11/2011 | Millerd |
| 9,694,140 | B2 | * | 7/2017 | Rubinstein .......... A61M 5/3245 |
| 2002/0004650 | A1 | * | 1/2002 | Kuracina ............ A61M 5/3243 604/198 |
| 2005/0096599 | A1 | | 5/2005 | Crawford et al. |
| 2006/0229562 | A1 | | 10/2006 | Marsh et al. |
| 2010/0298770 | A1 | * | 11/2010 | Rubinstein ............ A61M 5/326 604/110 |
| 2011/0077600 | A1 | * | 3/2011 | Uchida ................. A61M 5/326 604/198 |
| 2011/0257603 | A1 | * | 10/2011 | Ruan .................... A61M 5/326 604/198 |
| 2011/0270198 | A1 | * | 11/2011 | Perot .................... A61M 5/326 604/198 |
| 2011/0295204 | A1 | | 12/2011 | Bang |
| 2013/0190721 | A1 | * | 7/2013 | Kemp ................. A61M 5/2033 604/506 |
| 2014/0323979 | A1 | * | 10/2014 | Henley ............... A61M 5/2033 604/198 |
| 2015/0011944 | A1 | * | 1/2015 | Young ................ A61M 5/2033 604/198 |
| 2015/0273162 | A1 | * | 10/2015 | Holmqvist .......... A61M 5/2033 604/111 |

FOREIGN PATENT DOCUMENTS

| | | |
|---|---|---|
| EP | 2090326 A1 | 8/2009 |
| WO | 03041770 A2 | 5/2003 |
| WO | 2006123251 A2 | 11/2006 |
| WO | 2013121307 A1 | 8/2013 |

OTHER PUBLICATIONS

International Search Report and Written Opinion of the International Searching Authority dated May 26, 2014, issued in Application No. PCT/PL2013/050024.

Written Opinion of the International Preliminary Examining Authority dated Sep. 4, 2015, issued in Application No. PCT/PL2013/050024.

Notification of Transmittal of the International Preliminary Report on Patentability dated Jan. 21, 2016 issued in Application No. PCT/PL2013/050024.

* cited by examiner

SAFETY NEEDLE DEVICE

BACKGROUND OF THE INVENTION

Field of the Invention

The invention relates to a safety needle device which is mounted onto an outer medical instrument and which is a disposable device, assuring a user protection against an accidental or intentional prick with a needle before and after a proper use of the device in compliance with the purpose for which it is intended, and which device can be provided with an adjustment of the insertion depth of the needle into a patient's body.

State of Art

There are known safety needles serving to introduce into the patient's body a dose of a cosmetic and/or pharmaceutical composition which is being drawn out of a container disposed in an injection device cooperating therewith, which usually comprises a mechanism for the dose adjustment. The safety needle should be a disposable device, replaceable after every administration of a medicine dose, for example, insulin, human somatotropin or medicines against osteoporosis, and should be safe for circumambiency, that is protective against an accidental injury of the user both before its primary use, and after, that is protective against an accidental injury by the contaminated needle used earlier. After use safety needles are retracted from the patient's body and removed from the medical instrument after single use in order to minimize impurity of medicine closed in the container and to prevent a re-use of the needle. The user of a safety needle device is a medical professional, or another caregiver, but also more and more frequently an individual patient making a choice of the medicine dose, following doctor's prescriptions, and adjusting the medicine dose, for example insulin, respectively to a result of a blood sugar level test performed by himself, and then making by himself the injection of the medicine dose. However, a danger of a needlestick injury relates also to every person who may be in touch with the needle after it has been thrown away by the user, including the activities of packaging of the devices used, safeguarding, transport and the process of utilization. As for an angle at which the needle enters the patient's body, it has been observed that the injection "at a sharp angle" is very often practiced in health centers, in which needles with a nominal length of 8 mm are used. In the case when patient's predispositions require an application of a shorter needle, the hospital staff applies an injection technique "at the sharp angle", which results in different actual insertion depths depending on the needle inclination. Such a method, of making the injection "at the sharp angle" to the patient's body surface, is the preferred and convenient method also because of ergonomic reasons. However, in case of hypodermic injections of insulin or preparations used in cosmetic medicine, for example anti-wrinkle agents, performed by needles or particularly thin cannulas, the injection technique "at the sharp angle" applied by using known safety needle devices often leads to bending of the needle during and in the course of its insertion into the skin. Such a warped needle precludes the proper and precise application of the administered substance and may be dangerous for the patient.

Known safety needle devices have complex structure requiring precise cooperation of many component parts, which is the reason why these devices are not only costly but also, because of their complexity, susceptible to damages and faulty in operation, which may be dangerous for the user. In known safety needle devices, observing a needle end from the patient's side by the user before the use of the device is neither easy nor convenient, and in most cases impossible. Likewise in the course of preparing the needle for use, which requires evacuation of air lingering in the bore of the needle. In the known devices adequate preparation of the device for the use is not possible.

The known safety needles do not provide the user with the comfort of checking whether the appearance of the needle is correct, of checking its alinement and patency before the use as well as checking whether the needle bore is full of liquid which is to be administered to the patient, wherein the use of the device with a defective needle or the fact of introducing into the patient's body a certain amount of air, because of the incorrect preparation of the needle for the use, causes a serious threat for the patient.

The safety needle, especially its end from the patient's side, should be shielded before its primary use but also, immediately, after its withdrawal from the patient's body, still before the removal of the whole safety needle device from the medical instrument. At the same time, the needle should be guided in the course of the use of the device in such a manner as to enable its insertion into the patient's body "at the sharp angle" simultaneously assuring the correct insertion and injection as well as safety for the patient, independently of parameters of the needle or cannula.

It is desirable to design a cheap safety needle device of simple structure precluding a subsequent use of the device after its single use.

From patent description no. U.S. Pat. No. 7,815,611 B2 there is known an insulin safety needle device comprising a hub for fixing to an injection device, a needle mounted in the hub with one end for insertion into a container with insulin and with another end adapted to the injection into the patient's body, a protecting shield surrounding the needle and movable along its axis, which is being locked after the use of the device in the position, in which it protects a needle tip, and further the device comprises a catch pawl attached to the hub and called a clip member, with resilient side tongues, and a spring disposed inside the protecting shield. The resilient side tongues of the catch pawl, starting from the moment of assembling of the safety needle device until the moment of the device activation, are biased, which may, as a result of long-lasting storage of the device or transportation, cause a permanent deformation of the side tongues and prevent the locking of the protecting shield from activating after the use of the device, and thereby impending the needle protection. The threat is the more serious as the side tongues of the catch pawl are structure elements of rather small dimensions and as such they undergo deformations more easily. In this device, the spring acts by being expanded between the protecting shield and the catch pawl with the resilient side tongues. In this way, the spring acts directly onto the locking means additionally increasing their deformation and having an adverse impact on the locking effectiveness. If the needle is not correctly protected after the use of the device, such a device may be re-used. In this safety needle, the user has an easy access to the side tongues of the catch pawl, which gives him or her a possibility to unlock the protecting shield easily and to expose the needle, for the purpose of its repeated or multiple use. The structure of this safety needle does not enable the assessment of the state of the needle including its patency, which is a discomfort for the user and may even result in not administering the medicine to the patient because the user is not able to assess whether the flow through the needle during the injection is effective or not. The angle, at which the device is applied to the patient's skin and the injection is made, is another issue. The protecting shield in this device has the end from the patient's side of a relatively big surface, which forces the injection of the needle at the right angle to the patient's skin. Every possible change of the device arrangement relative to the patient's body surface towards the angle different than the right angle causes a significant shortening of the declared insertion depth and thereby a defective injection, and a necessity to perform a corrective injection to supply the respective medicine dose, and this in turn requires a further or another precipitated injection, and the use of another disposable device. In the described safety needle device, the side tongues of the catch pawl, after locking the protecting shield in the position shielding the needle after the use of the device, function also as indicators of the use of the device. However, the feature that the indicator of the use of the device is situated on locking means and is accessible for the user, who may easily change the indication of the state of the use of the device, is an undesired feature.

From patent description no. U.S. Pat. No. 8,062,265 B2 there is known an insulin safety needle having a hub enabling the attachment of the safety needle to an injection device, a cannula mounted in the hub with one end puncturing a container with insulin and with the other injection end, a protective shield slidable to a position preventing a re-use of the safety needle. The movement of the protecting shield along the hub is associated with its rotational movement which is forced by a specifically designed opening. The rotational movement of the protecting shield is an undesired movement because the shield contacts directly with the patient's skin during the injection and a friction thereon may produce an additional impediment to a correct operation of the device, as well as may cause the patient additional unpleasant and undesired impressions. In the described safety needle it is required to remove, before the use, an additional component part shielding the needle and protecting against an accidental actuation of a blocking. As soon as it is removed, there is a possibility to cut oneself with a non-protected cannula repeatedly because the actuation of the blocking of the protecting shield is performed only when a significant determined length of the cannula is exposed. This safety needle involves the necessity to use a metal spring pushing out the protecting shield because during the storage period of the product before use, the safety needle is subjected to load, and the spring made of plastic would deform permanently, and would not be able to cause the full movement of the protecting shield necessary to protect the needle. The application of the metal spring is a drawback because of economical and recycling reasons.

Patent description no. EP 2,090,326 discloses a safety needle with a protecting shield, the blocking of which in a position preventing a re-use of the needle requires meeting two conditions. Firstly, the injection has to be performed with a full possible depth so that the protecting shield is able to reach a container with a spring. Secondly, the injection has to be performed with an adequate force so that the protecting shield is able to break off safeguard locking against self-actuation in the container with the spring. In this safety needle device there is a possibility to make repeated accidental or intentional injections provided that injections are not made with full depth or are made with a force insufficient to actuate the blocking. A necessity to exert onto the protecting shield a big additional force indispensable to actuate the blocking may cause a discomfort for the patient, especially when he or she makes the injection on their own. This safety needle requires the application of the spring made of metal because during the period of product storage before use this safety needle is subjected to a load, and the spring made of plastic in this mechanical system would deform and as such would not cause a full movement of the protecting shield necessary to expose the needle. The metal spring is undesirable because of economical and recycling reasons.

From patent description no. U.S. Pat. No. 5,944,700 there is known a pen needle with an adjustable insertion depth. The pen needle comprises a hub attaching the needle to the pen, a cannula mounted in the hub with an end pricking a container with a medicine and with an injection end, and an additional component part rotatably coupled with the hub. To adjust a desired insertion depth, the user has to cause this component part to rotate around the cannula by manipulation close to a tip, which puts him or her at risk of hurting themselves. Moreover, the necessity to perform a rotational movement of some component part within the needle device to the pen is mistakable for the patient because it may suggest adjustment of the value of the medicine dose in the pen, with which it cooperates. Such a structure may create a danger for the patient, particularly for the patient in the state of serious stress or weakness.

Further, the publication of application description no. US 2011/0295204 A1 discloses a tube assembly for controlling length of a syringe needle, which comprises an additional component part coupled to the needle for the purpose of adjustment of the insertion depth. The tube assembly for controlling the active length of the needle, after being used, may be re-coupled to a new needle and re-used. The assembly requires, however, while adjusting the insertion depth, manipulation in the vicinity of a non-protected needle tip. Further, the manipulation is performed by a rotational movement of the component part of the tube assembly, which may suggest the adjustment of the medicine dose to be injected.

SUMMARY OF THE INVENTION

Objects of the Invention

The object of the present invention is to work out a safety needle device of a structure precluding an accidental needlestick injury of any person being in contact with the device, particularly after use of the device, by providing a device with a needle end from a patient's side shielded before the primary use of the device and with a self-activating shield of this needle end, which activates immediately after its withdrawal from the patient's body, yet prior to removal of the device in its entirety from a medical instrument. Protection of the needle end from the patient's side shall be performed without involvement of the user.

Another object of the invention is to design a safety needle device of a structure preventing the device from being re-used after a single use thereof.

It is yet another object of the present invention to provide a safety needle device enabling easy and convenient observation of the needle end from the patient's side prior to the use of the device in order to check the state of the needle end, that is its appearance and patency, and to prepare it for performing an injection or taking a body tissue, wherein the preparation of the needle consists in expelling air from the needle interior. Priming of the needle is always recommended to be made in such a manner that prior to the use of the device a small amount of liquid is being expelled from the needle in order to ensure that no air bubbles are entrapped within a bore of the needle. This is very important for the patient's safety. At the same time, for the patient's comfort, examination of the needle during INSERTION PHASE, INJECTION or TAKING PHASE and RETRACTION PHASE should be rendered difficult.

The object of the invention is to design a safety needle device, having a high operational reliability, by developing a construction in which none of the component parts are pre-biased or loaded before activation of the device, and in particular locking means for locking the device against a re-use.

The object of the invention is also to design a construction, in which locking means for locking the device against re-use of is inaccessible for the user, rendering destruction of blocking in order to re-use or multiple use of the device impossible for him or her.

Another object of the invention is to design a safety needle device of a construction enabling performance of an injection of a medicine with the needle being inserted into the patient's body also "at the right angle", which is being the angle more convenient for and preferred by the patients and/or health care professionals, simultaneously guaranteeing that the insertion depth which is, on one hand, declared in the given device and, on the other hand, required by an individual patient is secured. The construction of the device should be of such a design that in the course of inserting the needle into the patient's body and during the injection a component part shielding the needle would receive the load originating from the contact with the body and the needle would be unloaded entering the patient's body freely.

The object of the invention is to provide a safety needle device with an indicator of the state of use of the device informing that the device is safe to be used. A structure of the device should preclude the user from manipulating the indicator in order to change the indication of the state of use of the device.

Yet another object of the invention is to work out a safety needle device of a construction in which movable component parts realize movements longitudinal or transverse relative to the axis of the needle, without any rotatable movements in relation to the needle axis.

Further object of the present invention is to design a safety needle device of a construction which does not require an application of metal springs or which is completely devoid of metal springs in order to reduce further production costs of the final product and to facilitate the device utilization after use, which is of primary importance in case of devices intended for mass medical applications.

Another important object of the invention is to design a universal safety needle device with easy, safe and reliable regulation of an insertion depth, and with easy correction of this depth when a need occurs, and with an indication of a chosen insertion depth.

Yet another object of the invention is to provide a safety needle device of a simple structure comprising possibly a small amount of component parts in order to reduce manufacturing costs of the final product.

The objects set have been fulfilled in the present invention which is presented below.

THE INVENTION

A safety needle device according to the invention, for connection with a medical instrument to insert a needle into a patient's body to a determined insertion depth for injection of a cosmetic and/or pharmaceutical composition or for taking a tissue sample, especially a bodily fluid sample, comprises
- a hub with fixing means for fixing said device onto the medical instrument,
- a needle mounted in said hub and having a proximal end for engagement with the medical instrument and a distal end for insertion into the patient's body,
- a protecting shield movable longitudinally to an axis of said needle between an initial position in a pre-use state of said device and a final position in an after-use state of said device, in both states said distal end of said needle is protected,
- longitudinal resilient means disposed between said hub and said protecting shield and acting longitudinally to said axis of said needle,
- a housing movably mounted onto said hub and slidably carrying said protecting shield, and
- transverse resilient means disposed within said housing and acting transversely relative to said axis of said needle, said device having technical means configured for cooperation with each other, respectively,
- retaining means disposed on said protecting shield, said housing, said transverse resilient means and on said longitudinal resilient means for retaining said protecting shield in said initial position,
- locking means against re-use of said device disposed on said protecting shield and on said transverse resilient means for locking said protecting shield in said final position,
- guiding means of said locking means against re-use of said device disposed on said protecting shield for guiding said locking means against re-use of said device during use of said device,
- locating means of insertion depth, first and second, disposed, respectively, on said hub and on said housing for locating a position of said housing relative to said hub longitudinally to said axis of said needle, said position corresponding to said determined insertion depth,
- adjustment means of insertion depth, movable and immovable, disposed, respectively, on said housing and on said hub for changing said position of said housing relative to said hub longitudinally to said axis of said needle and for changing an adjustment of an insertion depth,
- indication means of insertion depth adjustment disposed on said housing and on said hub for indicating an adjustment of an insertion depth,
- indication means of state of use of said device disposed on said protecting shield and on said housing for indicating the state of use of said device, wherein
in order to assure that changing of the adjustment of the insertion depth is performed by displacing said movable adjustment means of insertion depth exclusively longitudinally and transversely relative to said axis of said needle, said housing is configured so that it is elastically deformable in direction perpendicular relative to said axis of said needle for changing said adjustment of said insertion depth.

Preferably, said adjustment means of insertion depth is configured so that it enables multiply changing of said adjustment of said insertion depth from the adjustment of the smallest insertion depth to the adjustment of the biggest insertion depth and from the adjustment of the biggest insertion depth to the adjustment of the smallest insertion depth.

Preferably, said movable adjustment means of insertion depth comprises on said housing, arranged circumferentially and opposite to one another, two adjustment lugs, and arranged circumferentially with circumferential displacement by 90° relative to said two adjustment lugs, at least one catch, and comprises on said hub, disposed opposite to said catch, at least one set of, arranged longitudinally one after another, at least two positioning teeth.

Preferably, said housing is disposed onto said hub between set positions within a set travelling range relative to said hub longitudinally to said axis of said needle, wherein said set positions correspond to said determined insertion depths and said set travelling range corresponds to a determined range of said insertion depth.

Preferably, for insertion of said needle to said determined insertion depth, said protecting shield is moved in a proximal direction to an extreme pressed position relative to said hub and said housing, wherein blocking of said device against re-use is irreversibly actuated when said distal end of said needle moves out of a distal surface of a distal end of said protecting shield in the course of movement of said protecting shield in said proximal direction, and for reliable locking of said protecting shield in said final position and for permanent locking of said device against re-use, said locking means against re-use of said device cooperating with said longitudinal resilient means is configured so that it locks a movement of said transverse resilient means in direction perpendicular to said axis of said needle after single use of said device, and locking means against re-use of said device is covered by said housing so that it is invisible and inaccessible for a user before, during and after use of said device.

Preferably, said protecting shield between said initial position and said final position moves exclusively longitudinally relative to said axis of said needle.

Preferably, in said initial position of said protecting shield in said pre-use state of said device, said longitudinal resilient means and said transverse resilient means are unbiased.

Preferably, in said final position of said protecting shield in said after-use state of said device, said longitudinal resilient means and said transverse resilient means are biased.

Preferably, for locking said protecting shield in said final position, said locking means against re-use of said device is displaced exclusively, respectively, longitudinally and transversely relative to said axis of said needle.

Preferably, said first locating means of insertion depth comprises arranged circumferentially at least one set of arranged longitudinally one after another at least two positioning teeth and said second locating means of insertion depth comprises arranged circumferentially at least one catch.

Preferably, said housing is configured so that said positioning teeth and said catch perform a function of, respectively, said first and said second locating means of insertion depth or a function of said adjustment means of insertion depth, depending on an operation phase of said device.

Preferably, said indication means of insertion depth adjustment comprises a scale on said housing and an indication tongue on said hub.

Preferably, said indication means of state of use of said device is configured so that it is observable and inaccessible for said user before, during and after use of said device.

A safety needle device according to the invention, for connection with a medical instrument to insert a needle into a patient's body to a determined insertion depth for injection of a cosmetic and/or pharmaceutical composition or for taking a tissue sample, especially a bodily fluid sample, comprises a hub with fixing means for fixing said device onto the medical instrument, a needle mounted in said hub and having a proximal end for engagement with the medical instrument and a distal end for insertion into the patient's body, a protecting shield movable exclusively longitudinally to an axis of said needle between an initial position in a pre-use state of said device and a final position in an after-use state of said device, in both states said distal end of said needle is protected, longitudinal resilient means disposed between said hub and said protecting shield and acting longitudinally to said axis of said needle between said initial position of said protecting shield, in which said initial position said longitudinal resilient means is unbiased, and said final position of said protecting shield, in which said final position said longitudinal resilient means is biased, a housing immovably mounted onto said hub and slidably carrying said protecting shield, and transverse resilient means disposed within said housing and acting transversely relative to said axis of said needle, said transverse resilient means in said initial position of said protecting shield being unbiased and in said final position of said protecting shield being biased, said device having technical means configured for cooperation with each other, respectively, retaining means disposed on said protecting shield, said housing, said transverse resilient means and on said longitudinal resilient means for retaining said protecting shield in said initial position, locking means against re-use of said device disposed on said protecting shield and on said transverse resilient means and movable exclusively, respectively, longitudinally and transversely relative to said axis of said needle for locking said protecting shield in said final position, guiding means of said locking means against re-use of said device disposed on said protecting shield for guiding said locking means against re-use of said device during use of said device, indication means of state of use of said device disposed on said protecting shield and on said housing, being observable and inaccessible for a user before, during and after use of said device, for indicating the state of use of said device, wherein for insertion of said needle to said determined insertion depth, said protecting shield is moved in a proximal direction to an extreme pressed position relative to said hub and said housing, wherein blocking of said device against re-use is irreversibly actuated when said distal end of said needle moves out of a distal surface of a distal end of said protecting shield in the course of movement of said protecting shield in said proximal direction, and wherein for reliable locking of said protecting shield in said final position and for permanent locking of said device against re-use, said locking means against re-use of said device cooperating with said longitudinal resilient means is configured so that it locks a movement of said transverse resilient means in direction perpendicular to said axis of said needle after single use of said device, and said locking means against re-use of said device is covered by said housing so that it is invisible and inaccessible for a user before, during and after use of said device.

Preferably, said device has locating means of insertion depth, first and second, disposed, respectively, on said hub and on said housing for locating a position of said housing relative to said hub longitudinally to said axis of said needle, said position corresponding to said determined insertion depth.

Preferably, said first locating means of insertion depth comprises arranged circumferentially at least one positioning tooth and said second locating means of insertion depth comprises arranged circumferentially at least one aperture.

Preferably, said device has information means of insertion depth disposed on at least one component part chosen from a group comprising said housing and said protecting shield.

Preferably, a distance between said distal surface of said distal end of said protecting shield and said distal end of said needle, in said initial position of said protecting shield, is different from a distance between said distal surface of said distal end of said protecting shield and said distal end of said needle, in said final position of said protecting shield, and preferably is bigger.

Preferably, said hub and, said longitudinal resilient means or said transverse resilient means, or said hub and said longitudinal resilient means and said transverse resilient means, or said longitudinal resilient means and said protecting shield, or said hub and said longitudinal resilient means and said protecting shield, or all component parts mentioned in this claim are integrally formed during a technological process as a single continuous part.

Preferably, said retaining means for retaining said protecting shield in said initial position comprises a detent of at least one trigger on said protecting shield, at least one abutment surface on said housing, a distal detent of at least one catch pawl on said transverse resilient means and said longitudinal resilient means.

Preferably, said longitudinal resilient means comprises a coil spring.

Preferably, said locking means against re-use of said device comprises at least one locking opening and at least one trigger on said protecting shield, and at least one catch pawl on said transverse resilient means, and guiding means of said locking means against re-use of said device comprises at least one trigger and at least one guide on said protecting shield.

Preferably, said transverse resilient means is attached to at least one component part chosen from a group comprising said hub, said housing and said needle.

Preferably, said transverse resilient means comprises at least one elastic arm.

Preferably, said indication means of state of use of said device comprises at least one indicator on said protecting shield and at least one opening on said housing.

Preferably, for inspection of said needle during the manufacture process of said device and for control of patency and vent of said needle before the use of said device, said protecting shield is provided with a respectively configured viewing opening.

Preferably, said device has an outer casing housing said device before its use and receiving said device after its use in order to guarantee to a user safe operation and utilization.

BRIEF DESCRIPTION OF THE DRAWINGS

The subject matter of the present invention in a preferred and non-limiting variant of a device with an insertion depth adjustment is presented on drawings, FIGS. 1-20, wherein FIG. 20 shows the fragment of the device adequate for both variants of the device that is for the variant with the insertion depth adjustment and the variant with a fixed insertion depth.

The subject matter of the present invention in the preferred and non-limiting variant of the device with a fixed insertion depth is presented on drawings, FIGS. 1A-14A, wherein

DETAILED DESCRIPTION OF THE PREFERRED INVENTION EMBODIMENTS

Figure 1:
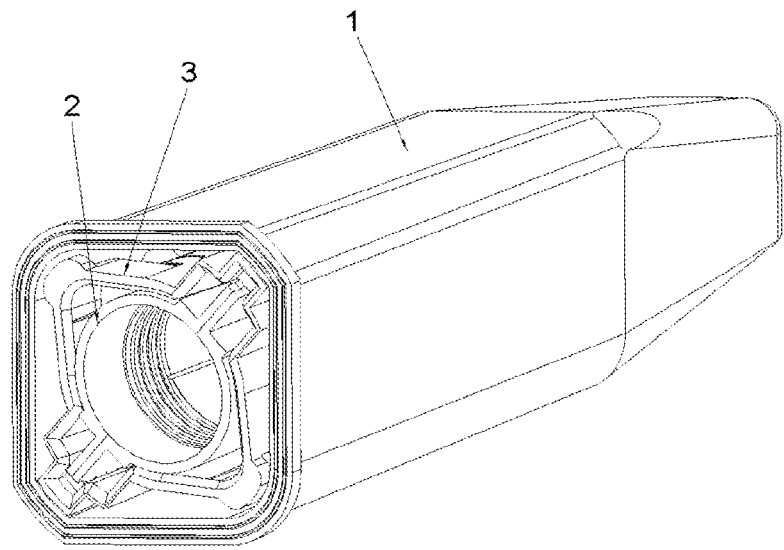
FIG. 1 shows a perspective view of an embodiment of a safety needle device in an outer casing 1, in the variant with the insertion depth adjustment, after taking it out of a protective packaging and after removal of a seal assuring a sterility barrier for the device (the protective packaging and the seal not shown)

A safety needle device according to the present invention cooperates with an outer medical instrument which can be an injection device such as a syringe serving to make injections, or a pen with a cartridge or with a container with a composition with a cosmetically and/or pharmaceutically active substance, or a device for taking samples of tissues, including bodily fluids, for example, blood. In particular, the present safety needle device cooperates with the pen for the injection once or for the injection of regular doses of a cosmetic and/or pharmaceutical composition. The present safety needle device can be provided with a needle or a cannula having thickness and length adapted, respectively, to an intended purpose of a use of the outer medical instrument cooperating with the present safety needle device, and, respectively, to the administered cosmetic and/or pharmaceutical composition. In case of medical instruments serving for subcutaneous injections, for example, for insulin injections or for injections of preparations used in a cosmetic medicine, for example, anti-wrinkle agents or cosmetic fillers for reducing worry lines, for example, preparations of botulinus toxin, the present safety needle device will be provided with the needle or the cannula thin and short. In order to minimize a pain, for subcutaneous injections of insulin there are desired the needles or the cannulas particularly thin and short, having thickness in a range from 29G to 32G that is from 0.23 mm to 0.25 mm, and the length in a range from 4 mm to 12 mm, in most cases from 4 mm to 8 mm. In case of the medical instruments such as syringes serving for intravenous injections or for intramuscular injections, the present safety needle device will be provided with the needle or the cannula, respectively, longer and thicker.

In the present description, for the sake of simplicity there will be used a term "a needle", which should be understood widely, without any limitation, as a needle or a cannula, suitable for the intended purpose of the device according to the present invention, for the cosmetic and/or pharmaceutical composition administered, and/or suitable for the cooperating outer medical instrument. The term "a needle or a cannula suitable for" encompasses a needle or a cannula of any parameters, properties, structure or material suitable for the intended purpose, such as a length, an outer diameter, a bore, a rigidity, a flexibility, a sharpened or not shape of both ends, a smoothness of an external surface, made of metal or plastic, etc.

The term "an insertion" occurring in the present description means an insertion of the needle or cannula into the patient's body, regardless of whether the end of the needle or cannula is pointed or not and regardless of whether the insertion is made to inject a cosmetic and/or pharmaceutical composition into the patient's body or to take a tissue sample, including a bodily fluid sample, from the patient's body.

In the present description, the terms "longitudinally", "longitudinal" and "transversely", "transverse" relate to the axis of the needle, and mean, respectively, "axially", "axial" relative to the axis of the needle, that is "parallel", "collateral" to the axis of the needle, and "across", "crosswise" or "perpendicularly", "perpendicular" to the axis of the needle, wherein the whole device extends, generally, more longitudinally to the axis of the needle, that is more along the axis of the needle, than transversely to it that is the whole device, generally, is longer than wider.

The terms "distal" and "proximal" in different expressions used in the present description relate, respectively, to the side "from the patient" and to the side opposite to the side "from the patient", that is to the side "from the outer medical instrument", regardless of that whether a particular structure element does contacts the patient's body or the outer medical instrument or does not. And therefore, for example, there will be mentioned a distal end of the needle, that is the end from the patient's side, which enters the patient's body during the insertion, wherein the distal end of the needle will be sharpened in case of the classic needle or will not be sharpened in case of the cannula penetrating a body or a skin. Then, a proximal end of the needle is the needle end from the medical instrument side, which is coupled with the medical instrument before use of the present device to perform an injection or a taking, respectively, to the cooperating outer medical instrument. When the outer medical instrument is a pen, for example, an insulin pen, then the proximal needle end will be coupled with or introduced into the cartridge or the dispensing container with insulin, being placed inside the pen.

Figure 2:
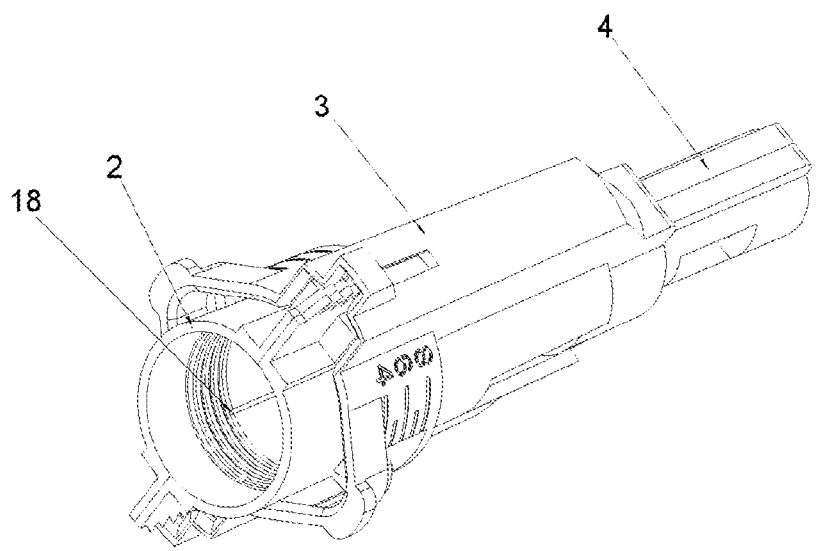
FIG. 2 shows a perspective view of the safety needle device, before use, after removal of the outer casing 1.
Figure 1A:
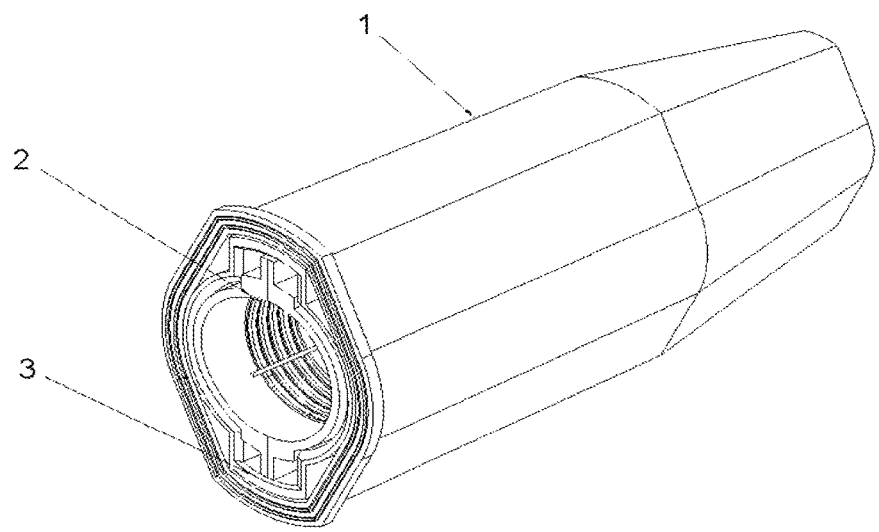
FIG. 1A shows a perspective view of an embodiment of the safety needle device in an outer casing 1, in the variant with a fixed insertion depth, after taking it out of a protective packaging and after removal of a seal assuring a sterility barrier for the device (the protective packaging and the seal not shown)
Figure 2A:
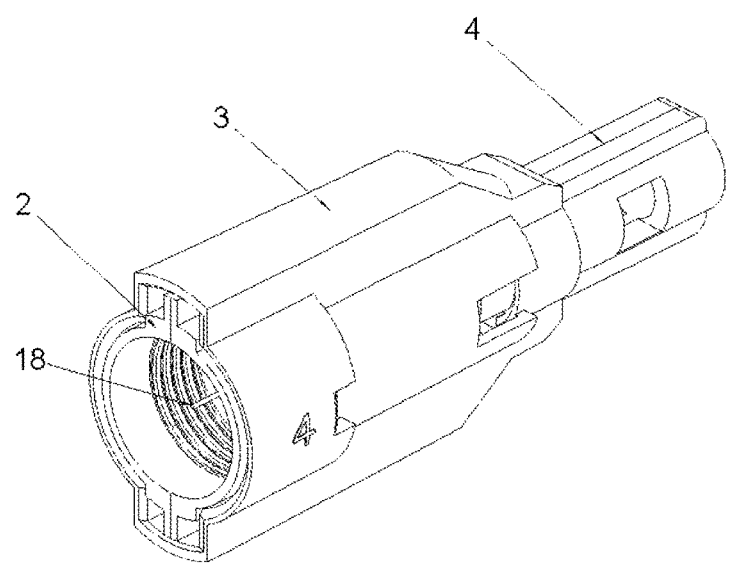
FIG. 2A shows a perspective view of the safety needle device, before use, after removal of the outer casing 1.

The safety needle device for the medical instrument, according to the present invention, in both variants that is with a fixed insertion depth and with an insertion depth adjustment, has a compact structure and, before mounting onto or after dismounting from the outer medical instrument, constitutes a separate, autonomous device, as shown, respectively, in FIGS. 2 and 2A.

In the following description of the safety needle device in both variants, the used expression "configured for cooperation with each other, respectively," means that individual of the mentioned technical means is configured for cooperation with the respective ones from the remaining of the mentioned technical means, wherein the used expression "configured for cooperation with each other, respectively," encompasses also the meaning "formed or shaped or arranged or designed suitably and adequately for cooperation" to perform correctly respective functions of individual technical means or component parts or structure elements of the component parts for the correct performance of the functions of the whole device. Similarly, the expression "configured so that" comprises the meanings "formed or shaped so that", "arranged so that" and "designed so that".

The Safety Needle Device in the Variant with the Insertion Depth Adjustment

The safety needle device, in an embodiment of the variant with the insertion depth adjustment, is presented in FIGS. 1-20.

The construction of the safety needle device with the insertion depth adjustment has been designed in order to provide, on one hand, the user of devices of this type with a device with a possibility to adjust the desired insertion depth from the range of much used insertion depths, depending on a place of the insertion or an obesity degree of the patient, and to eliminate, on the other hand, a necessity to supply a medical staff with a full range of the safety needle devices of different insertion depths. A choice of the insertion depth, individually according to current needs of the patient or to particular application of the device, is important for the patient's safety. In case of subcutaneous injections, the insertion depth has to be chosen such that to preclude from intramuscular injections.

Figure 3:
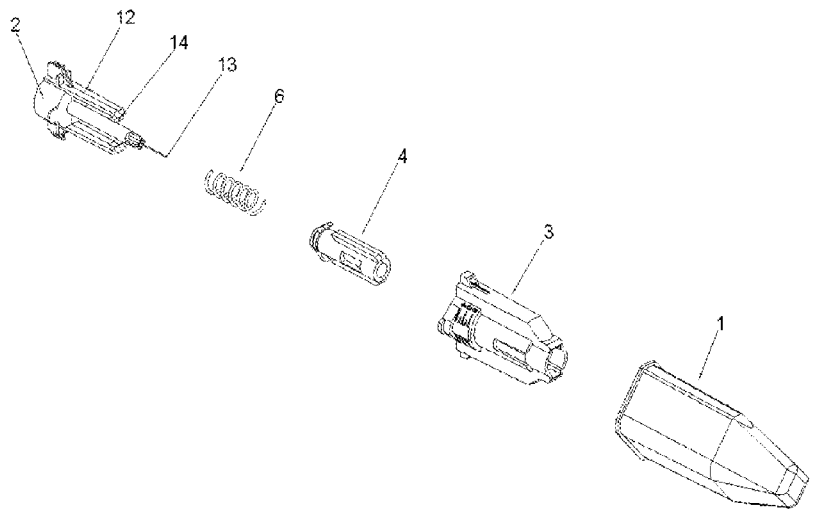
FIG. 3 shows an exploded perspective view of the safety needle device of FIG. 2.

On the whole, as shown in FIGS. 1-3, the safety needle device is constructed from a hub 2, a needle 11, a protecting shield 4, longitudinal resilient means 6, transverse resilient means 12 and a housing 3, which component parts together with situated thereon technical means are arranged and configured respectively to cooperate mutually with each other in order to perform different technical functions of the device.

FIG. 1 shows the device, in the form as it will be delivered to the user that is after removal from a protective packaging but still disposed in an outer casing 1, and after removal of a seal (not shown) ensuring a sterility barrier. The seal can be in the form of, for example, a sealed sticker or a plugged or screwed on cap. To guarantee to the user a safety operation and utilization, the outer casing 1 serves also as a receiver of the device after its use.

FIG. 2 shows the device after its removal from the outer casing 1. The safety needle device in order to use it that is to insert the needle 11 into the patient's body to the determined insertion depth to inject a cosmetic and/or pharmaceutical composition or to take a tissue sample, especially a bodily fluid sample, has to be mounted onto the outer medical instrument. FIG. 3 shows in an exploded view, the component parts of the device, after removal from the outer casing 1.

The hub 2 has, as shown in FIG. 2, the holder with known fixing means to fix, removably or non-removably, the device onto the outer medical instrument, for example, in the form of a thread. Other couplings with the medical instrument are also possible, such as a snapped fastening or an interference fit, in order to limit a contamination of a proximal end 18 of the needle 11 inserted into or coupled with the outer medical instrument, for example, into or with the insulin pen and, in particular, into an insulin container or a cartridge disposed therein.

Figure 5:
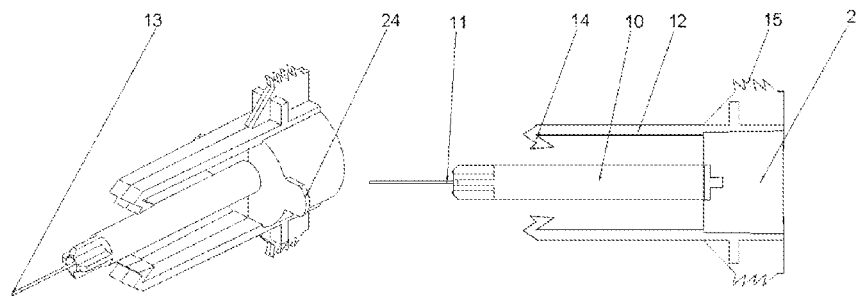
FIG. 5 shows perspective and side views of a hub 2 with elastic arms 12, positioning teeth 15, a needle 11 of the safety needle device of FIG. 2.
Figure 3A:
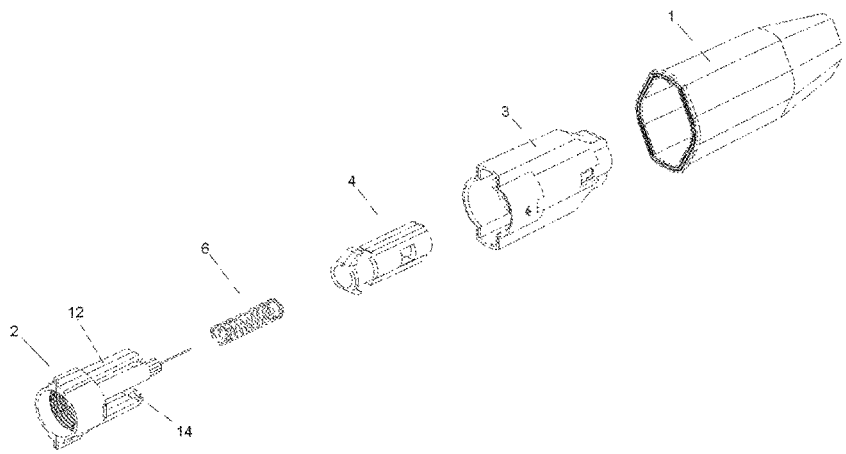
FIG. 3A shows an exploded perspective view of the safety needle device of FIG. 2A.
Figure 4A:
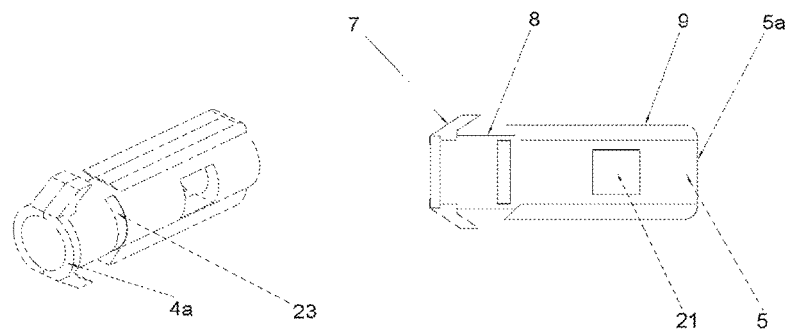
FIG. 4A shows perspective and side views of a protection shield 4 of the safety needle device of FIG. 2A.

In the hub 2, the needle 11 is fixedly mounted in the course of the technological process of injection moulding from a plastic or by other known techniques, for example, by gluing or by an interference fit. The needle 11 has the proximal end 18 to be coupled with the medical instrument, preferably, to be inserted into the medical instrument and a distal end 13 to be inserted into the patient's body. The needle 11 can be, on a portion of its length, supported by a support 10 attached to the hub 2, as shown in FIG. 5, for better supporting and for stable affixing the needle 11 on the hub 2. The support 10 together with the hub 2 can be made in the technological process of injection moulding of the plastic. The support 10 of the needle 11 can also constitute a component part of the device, which is not attached to the hub 2. The axis of the needle 11 is coaxial with the axis of an opening in the holder of the hub 2, see FIG. 5.

Figure 4:
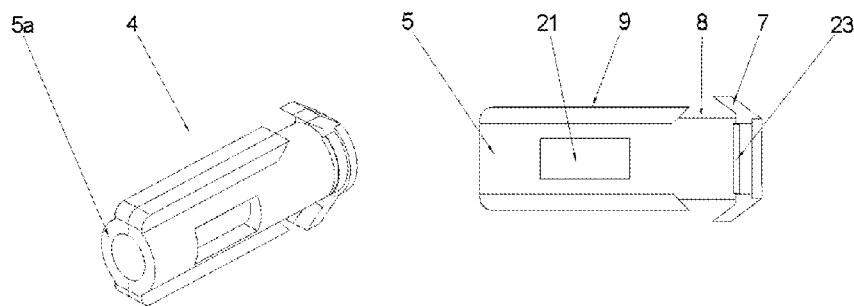
FIG. 4 shows perspective and side views of a protection shield 4 of the safety needle device of FIG. 2.
Figure 7:
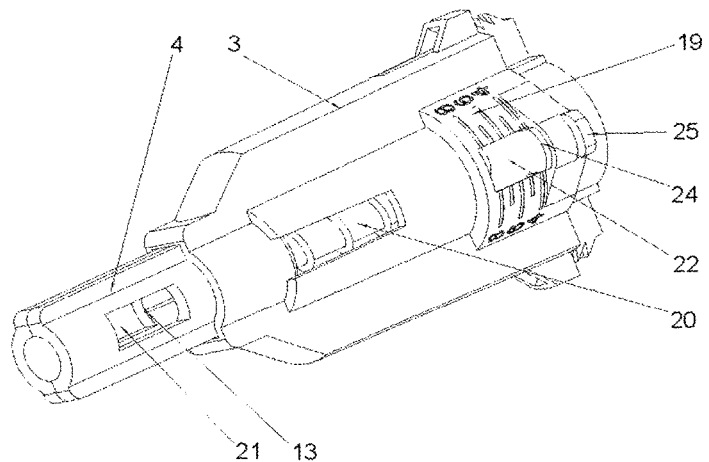
FIG. 7 shows a perspective view of the safety needle device from FIG. 2, prior to use, with an indicator 23 of a state of use of the device invisible in an opening 20.
Figure 8:
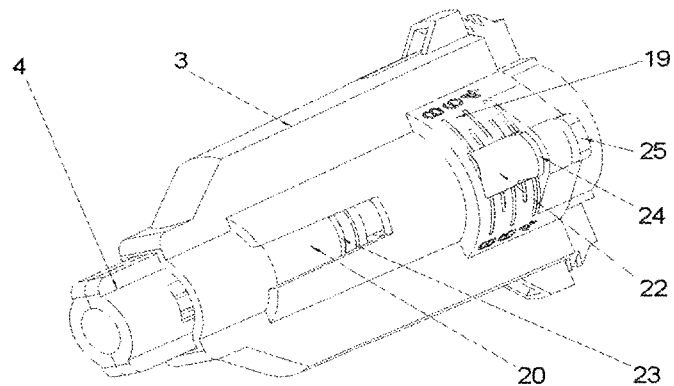
FIG. 8 shows a perspective view of the safety needle device from FIG. 2, after use, with the indicator 23 of the state of use of the device visible in the opening 20.

The protecting shield 4, as shown in FIG. 4, has essentially a tubular shape and is movable along the axis of the needle 11 between two stable positions, namely an initial position in a pre-use state of the device and a final position in an after-use state of the device. In both positions, the distal end 13 of the needle 11 is protected that is shielded by the protecting shield 4 to preclude the user from a possibility of an accidental injury. The protecting shield 4, during the use of the device, moves between the initial position and the final position, exclusively, longitudinally relative to the axis of the needle 11. The protecting shield 4 has two guides 9 configured to guide the protecting shield 4 in the housing 3 and to guide catch pawls 14 of locking means for locking the device against its re-use. The protecting shield 4 has two openings situated opposite each other, which constitute viewing openings 21 serving to control a presence or an absence of the needle 11, its coaxiality with the holder of the hub 2 and an appearance of the needle 11 in the course of a manufacturing process of the device, as well as to check a patency and a vent of the needle 11 prior to use of the device, as shown in FIGS. 7 and 8. The viewing opening 21 is configured so that it well shows the distal end 13 of the needle 11 before the use of the device but, at the same time, during the injection the needle 11 is well shielded, what is of utmost importance for persons who are scared of pricking with the needle.

Between the hub 2 and the protecting shield 4, the longitudinal resilient means are disposed, in the form of a spring 6, which acts along the axis of the needle 11, as shown in FIG. 3. The spring 6 may be a coil spring made of a metal or a plastic. The application of a non-metallic spring 6 is advantageous because of utilization aspects of the safety needle device after its use.

Figure 6:
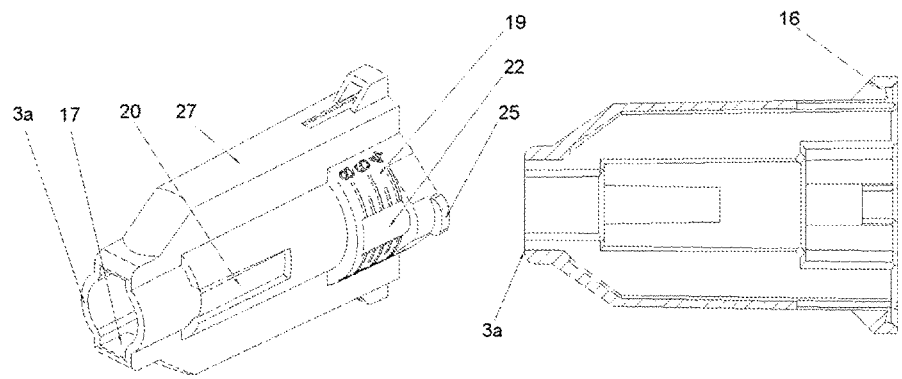
FIG. 6 shows a perspective view and a longitudinal cross-sectional of a housing 3 of the safety needle device of FIG. 2.

The housing 3, which is of an essentially tubular shape, is movably mounted onto the hub 2 and slidably supports the protecting shield 4. The protecting shield 4 is slidably borne inside the housing 3. As shown in FIG. 9, the longitudinal axis of the housing 3 is conforming to the axis of the needle 11. FIG. 6 shows that the housing 3 has two longitudinal protrusions 27, which facilitate to the user to screw the device with the hub 2 onto the outer medical instrument and unscrew it after the use of the device. The housing 3 has also two guiding grooves 17 which cooperate with the guides 9 of the protecting shield 4 to guide the protecting shield 4 between the initial position and the final position. The housing 3 is configured so that it is elastically deformable in a direction perpendicular relative to the axis of the needle 11.

In the variant of the device with the insertion depth adjustment, the housing 3 is movable onto the hub 2 between set positions within a set travelling range relative to the hub 2 along the axis of the needle 11, wherein the set positions correspond to the determined insertion depths and the set travelling range corresponds to the determined range of the insertion depths, for example, from 4 mm to 8 mm, as shown in FIGS. 7 and 8.

The transverse resilient means 12 in the form of two elastic arms 12 are coupled to the hub 2 opposite to each other and relative to the axis of the needle 11 on a distal side of the hub 2, which act transversally relative to the axis of the needle 11. In other preferred embodiments of both variants of the safety needle device according to the invention, the transverse resilient means 12, which generally are disposed inside the housing 3, can be engaged or coupled with the housing 3 or with the support 10 of the needle 11 or directly with the needle 11. The transverse resilient means 12 can be also engaged with each other by yet another structure element or structure elements such that to provide them or to enhance their elasticity, in case of more than a single elastic arm 12 or a form of these technical means different than the elastic arm 12. Thus, as the transverse resilient means every possible embodiment of technical means disposed inside the housing 3 should be understood provided it realizes functions as described in the present description. As shown in FIGS. 3 and 5, the elastic arms 12 are made together with the hub 2 as a single continuous part during the technological process of the injection moulding of the plastic. The elastic arms 12 and the hub 2, in the described embodiment of this variant of the device, constitute a single assembly part of the device as shown in FIGS. 3, 5, 9-19.

The construction of the safety needle device enables to manufacture also other its component parts as integrally formed during the technological process into a single continuous part from a homogeneous material, namely, the hub 2 and the spring 6, or the hub 2 and the spring 6 and the elastic arms 12, or the spring 6 and the protecting shield 4, or the hub 2 and the spring 6 and the protecting shield 4, or all mentioned component parts together that is the hub 2, the spring 6, the elastic arms 12 and the protecting shield 4. The structure of the device enables, therefore, to make the device consisting, when taking into account the housing 3, of four, of three, and even of two separate assembly parts. Moreover, during the manufacture of the component parts as integrally formed by technology of the plastic injection moulding, these component parts achieve equal deformations and dimensional deviations, depending on different parameters of the injection moulding. This enables to avoid a situation when during the manufacture process one of component parts is manufactured in an upper region of an acceptable dimensional tolerance and the other component parts, cooperating one, in a lower region of the acceptable dimensional tolerance. In this disadvantageous situation, according to design principles and manufacture technology, both component parts are correctly configured and manufactured, however, a likelihood of incorrect cooperation, for example, by keying, of these component parts increases considerably. This impacts on a reduction of reliability of the device and on an increase of a risk of injuring, performing the incorrect and/or painful insertion, injecting ineffectively a medicine. With a minimal number of the two separate assembly parts, the assembly of the device is very simplified.

There are different technical means disposed onto the hub 2, the protecting shield 4, the spring 6, the elastic arms 12 and the housing 3, which are arranged and configured suitably to cooperate mutually with each other in order to perform different technical functions of the device.

Figure 20:
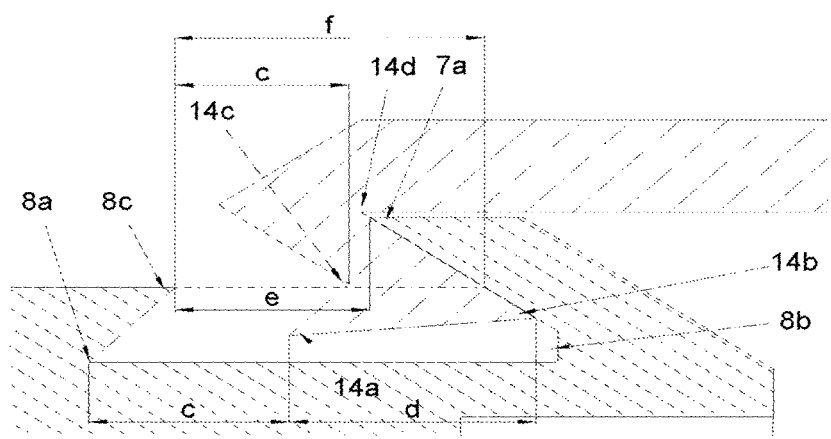
FIG. 20 shows, in enlargement, a fragment of a cross-sectional view of the engagement of locking means against re-use of the device, that is a locking opening 8 and the trigger 7 of the protection shield 4 with the catch pawl 14 of the elastic arm 12, in RETRACTION and LOCKING PHASE, after use of the device.

To retain, in a pre-use state of the device, the protecting shield 4 in the initial position, the device is provided with retaining means for retaining said protecting shield in the initial position, which comprises detents 7a on two triggers 7 on the protecting shield 4, two abutment surfaces 26 on the housing 3, distal detents 14a of the catch pawls 14 disposed on distal ends of the elastic arms 12 and the spring 6, see FIG. 9 and, auxiliary, FIG. 20.

Figure 19:
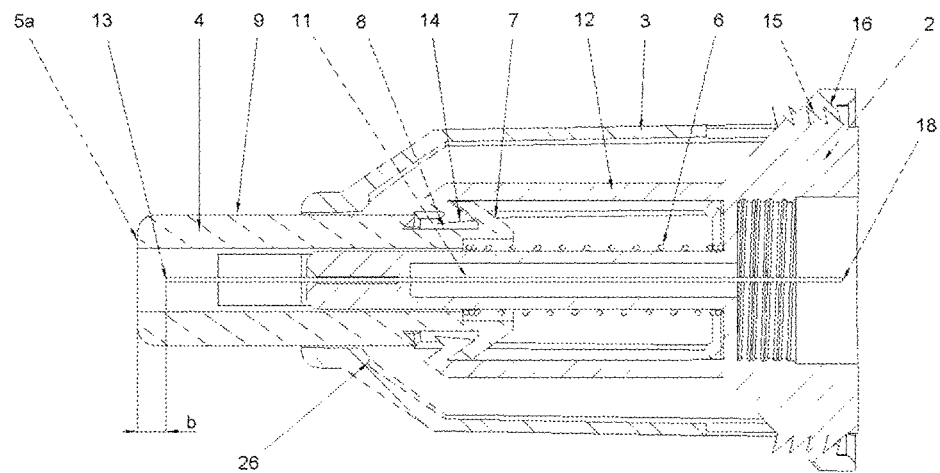
FIG. 19 shows the longitudinal cross-sectional view of the safety needle device from FIG. 2, in RETRACTION PHASE of the needle 11 from the patient's body and LOCKING PHASE of the device, with the protecting shield 4 in its final position after the use of the device, in which it is locked against a re-use.

For locking the protecting shield 4 in the final position and for precluding its movement along the axis of the needle 11, both in the proximal direction and in the distal direction, in the after-use state of the device, the locking means against re-use of said device is provided, which comprises two locking openings 8 and the two triggers 7 on the protecting shield 4 and the catch pawl 14 on the elastic arms 12, as shown in FIG. 19. The locking means against re-use of said device are displaced, during the use of the device, exclusively, respectively, longitudinally and transversally relative to the axis of the needle 11. The safety needle device is configured so that the housing 3 surrounds completely the locking means against re-use of said device, whereby the user does not see and has no access to the locking means against re-use of the device, neither prior to use of the device nor during any of functioning phases nor after a single use of the device, as shown in FIG. 9. The user is not able to observe and is not able to manipulate with the means in order to change its state or to destroy it in any of operation phases of the device. Such a structure precludes the user from destroying a blocking with the purpose of re-using or repeated using of the device, what would be dangerous for the patient. Another important future of the device is that the locking means against re-use of said device is free that is unbiased and not loaded during storage and during transport and is biased only during the use of the device. The locking means whereby retains its resilient characteristics regardless storage time, what ensures reliability of functioning of the blocking against re-use. Thanks to which, the device ensures a long term of usability with a guarantee of the proper functioning.

For guiding the locking means of the device against re-use, during the use of the device, guiding means of the locking means against re-use of said device is provided in the device, which comprises the two triggers 7 and the two guides 9 on the protecting shield 4. there is presented in FIGS. 15-18 and explained in the following description of the operation and functioning phases of the device.

For locating a position of the housing 3 relative to the hub 2 along the axis of the needle 11, which position corresponds to the determined insertion depth, locating means of insertion depth, first 15 and second 16, is provided in the device, which comprises, in the variant of the device with the insertion depth adjustment, respectively, two sets of, longitudinally arranged one by one on an external surface of the holder of the hub 2, several positioning teeth 15, preferably, four, as in the described embodiment of this variant of the device, and circumferentially arranged two catches 16 on the housing 3. Each of the catches 16 is positioned, in the device, opposite the set of the positioning teeth 15, with which it engages respectively to the chosen and adjusted determined insertion depth, see FIG. 9.

However, the housing 3 can be also fixedly attached to or mounted on the hub 2 by other known technical means including techniques such as an interference fit, gluing or coupling by a heat treatment, without any specifically formed other structure elements such as the locating means of insertion depth first 15 and the second 16 or similar. Moreover, although in the described preferred embodiments of both variants of the safety needle device, the position of the housing 3 relative to hub 2 is being directly correlated or reflected in the determined insertion depth, it should be noted that, also, by a change of the length of the housing 3 that is the change of its longitudinal dimension relative to the axis of the needle 11, separately from the location of the position of the housing 3 relative to hub 2, it is possible to influence on the insertion depth.

Figure 10:
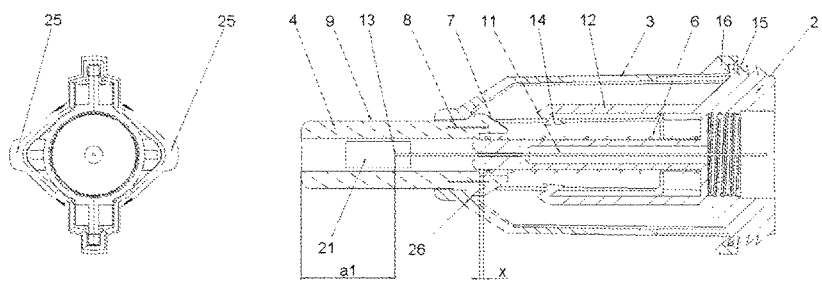
FIG. 10 shows a view from the side of a medical instrument, which is a proximal side that is opposite to "a patient's side", of the safety needle device of FIG. 2 and a longitudinal cross-sectional view of the device, with the initial adjustment of the smallest insertion depth, with the spring 6 unbiased, and with the protecting shield 4 in the initial position.
Figure 11:
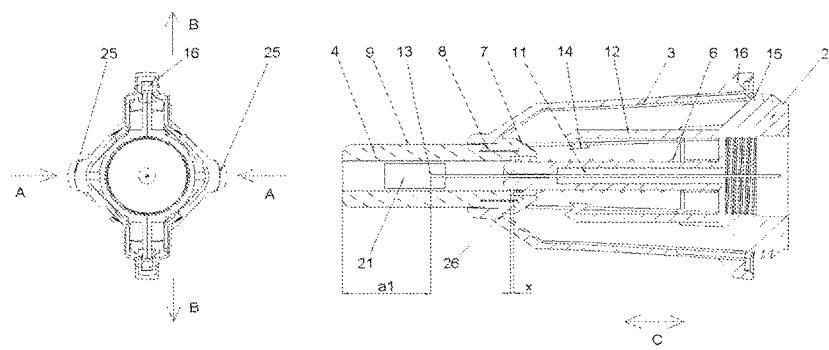
FIG. 11 shows a view from the medical instrument side, the proximal side that is opposite to "the patient's side", of the safety needle device of FIG. 2 and the longitudinal cross-sectional view of this device, in INSERTION DEPTH ADJUSTMENT PHASE with the initial adjustment of the smallest insertion depth, after the compression of adjustment lugs 25 with the purpose of changing the insertion depth adjustment.
Figure 10A:
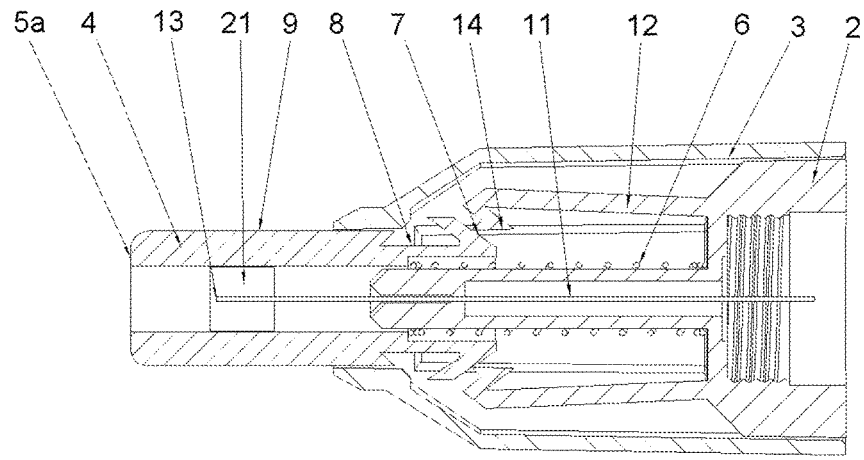
FIG. 10A shows a longitudinal cross-sectional view of the safety needle device of FIG. 2A, at the beginning of INSERTION PHASE after triggers 7 have come into contact with catch pawls 14.
Figure 11A:
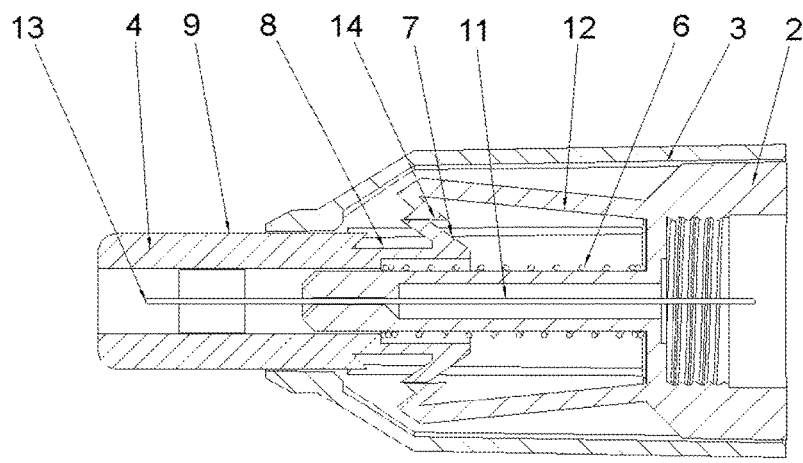
FIG. 11A shows a longitudinal cross-sectional view of the safety needle device of FIG. 2A, in INSERTION PHASE at the moment of moving away of the catch pawls 14 from an axis of the needle 11 by the trigger 7.

For changing the position of the housing 3 relative to the hub 2 along the axis of the needle 11 and for changing the insertion depth adjustment, adjustment means of insertion depth, movable and immovable, is provided in the device, as shown in FIGS. 10-11. The safety needle device in the variant with the insertion depth adjustment is configured such that during the change of the insertion depth adjustment in INSERTION DEPTH ADJUSTMENT PHASE, the user does not perform any rotational movement of any of the movable adjustment means of the insertion depth. The intention of the inventors of the device was to eliminate a possibility of making a mistake by the user between the insertion depth adjustment and the adjustment of a medicine dose on the outer medical instrument, for example, on the insulin pen. To change the medicine dose, for example, the insulin dose, conventionally a rotational movement of an adjustment part of the dose is reserved. The aim as posed herein by the inventors is important, because at present the user is in most cases the individual patient in his or her home environment, where, in case of aggravation of symptoms of a diabetic disease, the patient is left on his or her own resources and in this state he or she has to act quickly and precisely according to the operation manual of the safety needle device and the insulin pen. Therefore, in the variant of the present device with the insertion depth adjustment, the change of the insertion depth adjustment is realized only by longitudinal and transverse movements relative to the axis of the needle 11 of the movable adjustment means of the insertion depth, that is without any rotational movement relative to the axis of the needle 11. In order to ensure such realization of the change of the insertion depth adjustment, the housing 3 is configured so that it is deformable resiliently in the direction perpendicular relative to the axis of the needle 11 and it is movable relative to the hub 2 longitudinally relative to the axis of the needle 11. The movable adjustment means of the insertion depth comprises the housing 3 as itself and disposed thereon, arranged circumferentially and opposite to each other, two adjustment lugs 25, and, arranged circumferentially with the circumferential displacement by 90° relative to adjustment lugs 25, the two catches 16. The immovable adjustment means of insertion depth comprises, disposed on the hub 2, the two sets of, longitudinally arranged one by one, the several positioning teeth 15, preferably, as in the described embodiment of this variant of the device, of four positioning teeth 15. Each of the catches 16 during INSERTION DEPTH ADJUSTMENT PHASE is longitudinally displaced over the cooperating therewith set of the positioning teeth 15 until engagement with the positioning tooth 15 which is proper for the chosen and adjusted determined insertion depth.

In the variant of the device with the insertion depth adjustment, the housing 3 is configured so that the positioning teeth 15 and the catch 16 function as the adjustment means of the insertion depth in Phase 2 of the operation of the device, that is in INSERTION DEPTH ADJUSTMENT PHASE, and they also function as the locating means of insertion depth, respectively, the first 15 and the second 16, in Phases 1, 3, 4, 5 and 6 of the operation and functioning of the device, including, especially, the Phases such as INSERTION PHASE, INJECTION or TAKING PHASE, RETRACTION PHASE of the needle 11 from the patient's body and LOCKING PHASE of the device.

To indicate the insertion depth adjustment, indication means of insertion depth adjustment is provided in the device, which comprises a scale 19 on the housing 3 and an indication tongue 24 on the hub 2, as shown in FIGS. 2, 7-8.

For indication of the state of use of the device, that is the state of the device before use and the state of the device after use, indication means of state of use of the device is provided in the device, which comprises two indicators 23 on the protecting shield 4 and two openings 20 on the housing 3, see FIGS. 7-8. The opening 20 may be covered with a transparent plug. In the preferred embodiment, a pane of glass or a pane of plastic with resilient fixing means is snapped and/or pasted into the opening 20 of the housing 3, whereby the indication means of state of use of the device is observable but inaccessible for the user before, during and after use of the device. The word "observable" in the description of the present invention, should be understood in such a way that, dependently on the state of use of the device, the indicators 23 are invisible or visible in the openings 20. The indicators 23 are invisible in the openings 20 in the pre-use state of the device, and are visible in the openings 20 in the after-use state of the device. However, the user cannot interfere in the state or in a position of the indication means of the state of use of the device in none of the operation phases of the device.

OPERATION and FUNCTIONING PHASES of the Device in the Variant with the Insertion Depth Adjustment Phase 1—Preparation of the Safety Needle Device for Use, FIGS. 1-2, 7

The user removes from the outer casing 1 the seal ensuring a sterility barrier for the device (the seal not shown), takes off the device from the outer casing 1, FIGS. 1-2, and mounts the device by screwing the hub 2 onto the outer medical instrument.

The user, through the opening 20 in the housing 3 checks the state of the indicator 23 of use of the device on the protecting shield 4. In this operation phase of the device, the indicator 23 should not be visible in the opening 20 in the housing 3, see FIG. 7.

The user checks, through the opening constituting the viewing opening 21 which is specifically formed in the protecting shield 4, the state of the needle 11, which the distal end 13 is visible in the viewing opening 21, see FIG. 7. The control of the state of the needle 11 consists in checking its appearance, that is whether the distal end 13 of the needle 11 is straight and clean, as well as in checking its patency and in performing its vent. For this purpose, from the cartridge of the outer medical instrument, a small amount of the cosmetic and/or pharmaceutical composition intended to be injected should be forced into the bore of the needle 11 until a drop of this composition appears on the distal end 13. These preparatory measures will cause air lingering in the needle 11 to be expelled outside the needle 11, which is very important for the safety and comfort of the patient.

The device is delivered to the user with an initial adjustment of the insertion depth, which is the smallest insertion depth possible to be adjusted in the given device.

The length of the spring 6 is adapted respectively to the smallest insertion depth possible to be adjusted for the particular device that is the length of the spring 6 is matched in such a way that prior to use of the device and more precisely before a beginning of Phase 2, that is before INSERTION DEPTH ADJUSTMENT PHASE, the spring 6 is not pre-biased. This is advantageous for the patient because in case of a long time of storage of the device the correctness of its functioning is guaranteed. Such a structure of the safety needle device, with the spring 6 without the initial biasing, eliminates the necessity of application of the metal spring, which is very advantageous for economical and utilization reasons. The spring 6 can be made of a plastic, without any negative impact on the safety of the patient, even, in case of the safety needle device with a long term of usability. The spring 6 starts to be compressed only during the change of the initial adjustment of the insertion depth into a bigger insertion depth, that is during Phase 2 that is during INSERTION DEPTH ADJUSTMENT PHASE. The spring 6 is put under tension provided the change of the initial adjustment of the insertion depth into the bigger insertion depth is finally performed, or the spring 6 is put under tension only during Phase 3 that is during INSERTION PHASE with keeping the initial adjustment of the insertion depth that is with keeping the smallest insertion depth possible to be adjusted in the given device. The spring 6 remains biased after use of the device.

In this phase, in the pre-use state of the device, with the protecting shield 4 in the initial position, apart from the spring 6, also the elastic arms 12 are not biased, which involves similar advantages for the safety of an exploitation of the device as those described above in the context of the spring 6.

At the same time, before use of the device, the protecting shield 4 has a small pre-set range of a longitudinal travelling x, which, preferably, is from about 0.25 mm to about 0.50 mm, at a travel of the adjustment of the insertion depth amounting to 1 mm, FIGS. 9-10, wherein x is a distance between the spring 6 and the protecting shield 4 and, more precisely, between a distal end of the spring 6 and a bottom of a chamber receiving the spring 6 inside the protecting shield 4, FIGS. 9-10.

In this phase, in the pre-use state of the device, the protecting shield 4 is in its initial position relative to the hub 2 and to the housing 3 that is in such a position, in which the distal end 13 of the needle 11, that is the end from the patient's side of the needle 11, is in a distance a1 with a clearance x from a distal surface 5a of a distal end 5, that is the end from the patient's side, of the protecting shield 4, as shown in FIGS. 9-10, that is within the distance of a range (a1, a1-x), wherein the distance a1 corresponds to the adjustment of the smallest insertion depth as shown in FIGS. 9-10.

In this phase, that is with the protecting shield 4 in its initial position relative to the hub 2 and to the housing 3, the distal end 13 of the needle 11 is constantly visible in the viewing opening 21 in the protecting shield 4, which serves to control the state of the needle 11, FIGS. 7, 9-14.

Phase 2—Insertion Depth Adjustment, FIGS. 7, 9-14 and, in case of the outer medical instrument in the form of the injection device, the adjustment of the injected dose or a choice of the injection device with the proper dose of the cosmetic and/or pharmaceutical composition for administration The user starts with a reading of the initial adjustment of the insertion depth on the scale 19 of the device, which the initial adjustment of the insertion depth is the smallest insertion depth possible for adjustment in the particular device, FIGS. 7, 9-10.

In case of the necessity to change the initial adjustment of the smallest insertion depth onto the bigger insertion depth, the user presses onto the adjustment lugs 25 in the direction as shown in FIG. 11 by the arrows A, causing the housing 3 to be deformed resiliently in such a way that the catches 16 draw aside in the direction marked by the arrows B in FIG. 11. Every one of the catches 16 disengages from the corresponding set of the positioning teeth 15 on the hub 2, and the housing 3 can freely move longitudinally to another position relative to the hub 2. Then, firstly, the user moves the housing 3 in the proximal direction towards the side which is opposite to the side "from the patient" and, then, if there is a need for a correction of the adjustment of the insertion depth, in the direction chosen from the proximal and distal directions, shown in FIG. 11 by the arrows C, until the proper position of the indication tongues 24 on the hub 2 relative to the scale 19, respectively, to the final desired insertion depth that is to the final adjustment of the insertion depth, as shown in FIGS. 7 and 11-13. At the same time, the proper position of the indication tongues 24 on the hub 2 relative to the scale 19 corresponds to the engagement of every one of the catches 16 situated on the housing 3 in the proper position with the corresponding set of the positioning teeth 15 on the hub 2. The proper position of the indication tongues 24 and the proper position of the catches 16 relative to the set of the positioning teeth 15 corresponds to the chosen and adjusted determined insertion depth, see FIG. 9. With relation to FIG. 11, it is explained that the sign A—illustrates the direction of pressing onto the adjustment lugs 25 on the housing 3 in order to change the adjustment of the insertion depth, B—illustrates the direction of drawing the catches 16 on the housing 3 aside while performing the change of the adjustment of the insertion depth, C—illustrates the distal and proximal directions of the displacement of the housing 3 while performing the change of the adjustment of the insertion depth.

In the present safety needle device, the change of the insertion depth adjustment is realized only by longitudinal and transversal movements relative to the axis of the needle 11 of the movable adjustment insertion depth means that is of the housing 3, of the adjustment lugs 25 and of the catches 16, that is without any rotational movement of any component part of the device relative to the axis of the needle 11. To ensure such a realization of the change of the insertion depth adjustment, the housing 3 is designed such that it is elastically deformable in the direction perpendicular relative to the axis of the needle 11, namely the housing 3 is compressed towards the axis of the needle 11 in the region where the adjustment lugs 25 are situated thereon and is drawn aside from the axis of the needle 11 in the region where the catches 16 are situated thereon. In the described embodiment of the present safety needle device, the adjustment lugs 25, the housing 3 and the catches 16 do not realize any rotational movement relative to the axis of the needle 11.

Figure 12A:
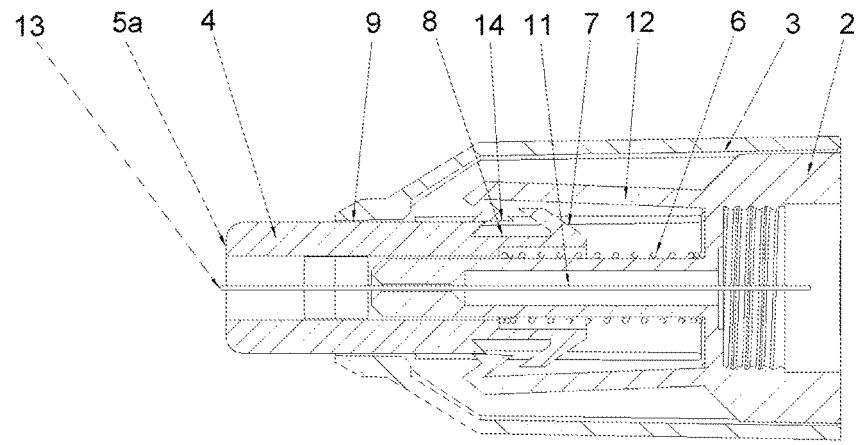
FIG. 12A shows a longitudinal cross-sectional view of the safety needle device of FIG. 2A, in INSERTION PHASE at the moment when a distal end 13 of the needle 11 from the patient's side is being commenced to be inserted into the patient's body.
Figure 12:
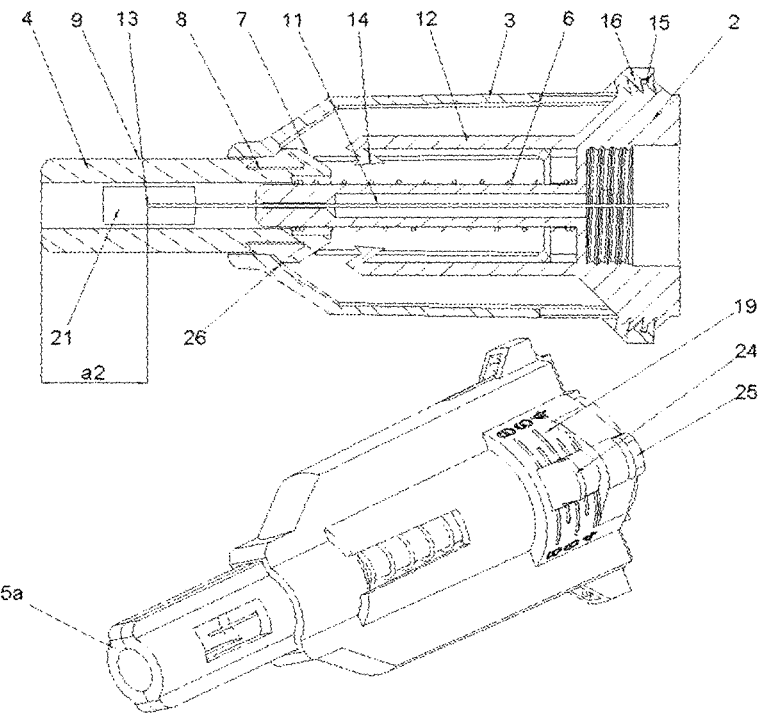
FIG. 12 shows perspective and longitudinal cross-sectional views of the safety needle device of FIG. 2, in INSERTION DEPTH ADJUSTMENT PHASE with one of intermediate insertion depths adjusted, with the spring 6 biased.
Figure 13:
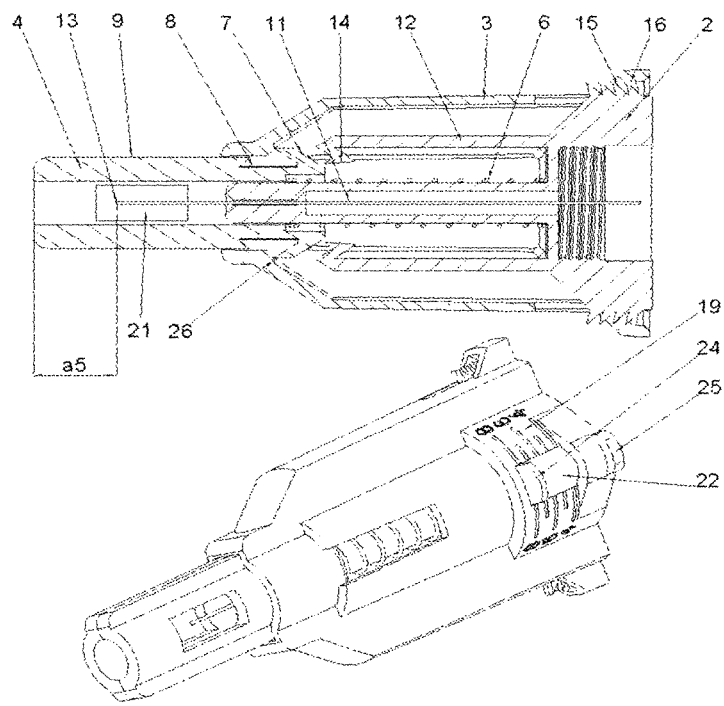
FIG. 13 shows perspective and longitudinal cross-sectional views of the safety needle device of FIG. 2, in INSERTION DEPTH ADJUSTMENT PHASE with the biggest insertion depth adjusted, with the spring 6 biased.
Figure 13A:
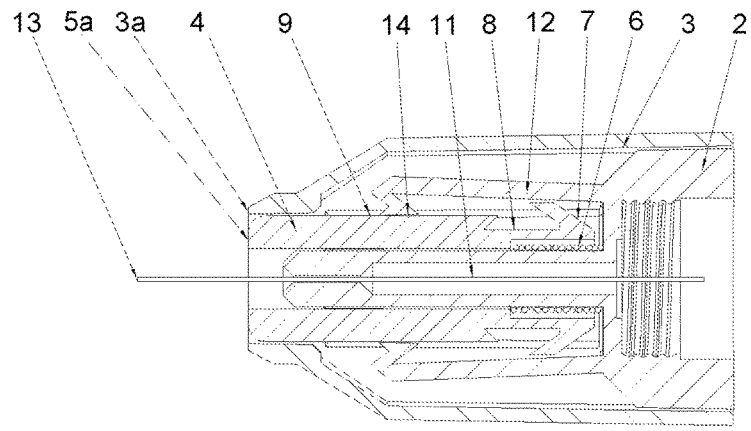
FIG. 13A shows a longitudinal cross-sectional view of the safety needle device of FIG. 2A, in INSERTION PHASE with the protecting shield 4 in its extreme pressed position relative to the hub 2 and to the housing 3, which position corresponds to an adjusted and performed full insertion depth.
Figure 14A:
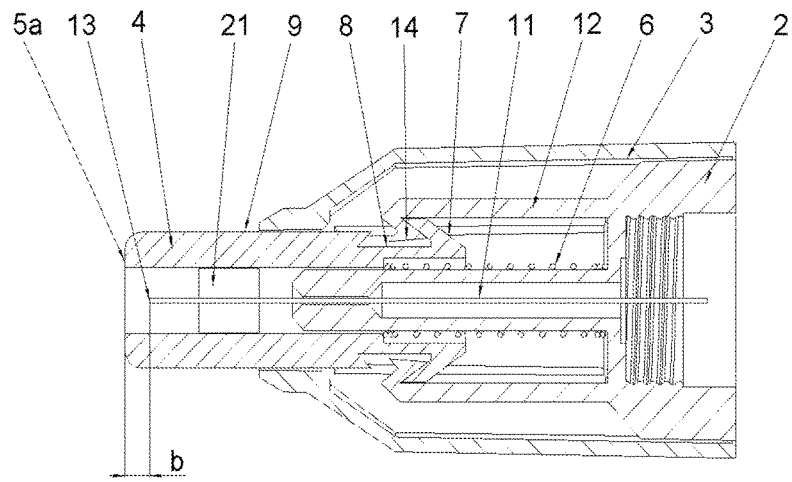
FIG. 14A shows a longitudinal cross-sectional view of the safety needle device of FIG. 2A, in RETRACTION PHASE of the needle 11 from the patient's body and LOCKING PHASE of the device, with the protecting shield 4 in its final position after the use of the device, in which it is locked against a re-use.
Figure 14:
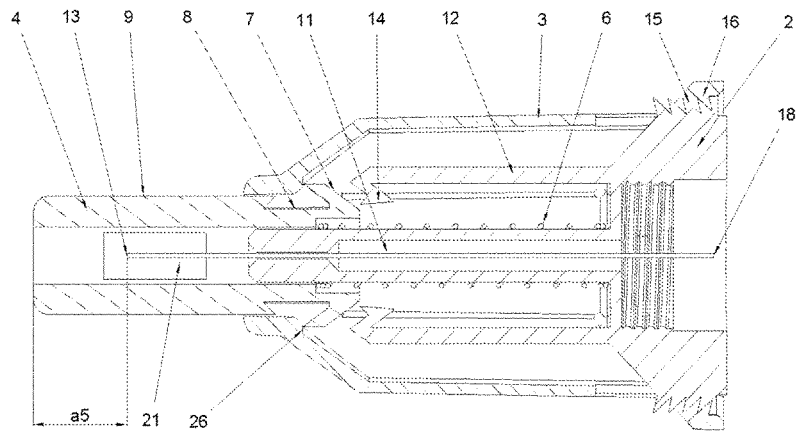
FIG. 14 shows a longitudinal cross-sectional view of the safety needle device of FIG. 2, in INSERTION DEPTH ADJUSTMENT PHASE with the biggest insertion depth adjusted, with the spring 6 biased.

In case of a necessity to change the initial adjustment of the smallest insertion depth into the bigger insertion depth, the protecting shield 4 is moved from its initial position together with the housing 3 to its position which corresponds to the chosen adjustment of the bigger insertion depth that is to such a position, in which the distal end 13 of the needle 11 is in a distance a2, a3 . . . aN, wherein N means a number of available determined insertion depths, and is equal to, for example, 5, that is N=5, from the distal surface 5a of the distal end 5 of the protecting shield 4, as shown in FIGS. 12-14. Simultaneously, the distance a2 corresponds to the adjustment of the second insertion depth being the first from intermediate insertion depths, as shown in FIG. 12, and the distance a5 corresponds to, as shown in FIGS. 13-14, the adjustment of the biggest insertion depth. Between the mentioned distances, there is a relationship as follows a1>a2>a3>a4>a5, that is a1 is bigger than a2 and a2 is bigger than a3 and so on.

In the present safety needle device, in the variant of the device with the insertion depth adjustment, in INSERTION DEPTH ADJUSTMENT PHASE, there is possible to change repeatedly the insertion depth adjustment from the adjustment of the smallest insertion depth to the adjustment of the biggest insertion depth and from the adjustment of the biggest insertion depth to the adjustment of the smallest insertion depth. The device is configured such that it enables to the user to carry out any correction of the insertion depth adjustment.

The positioning teeth 15 on the hub and the catches 16 on the housing 3 are configured so that the locating of the position of the housing 3 relative to the hub 2 and the locating of the adjusted insertion depth is secure. For this purpose, in the presented embodiment of the safety needle device of the variant with the insertion depth adjustment, the positioning teeth 15 and the catches 16 have surfaces which are respectively shaped as sloping and with which they mutually engage each other in such a way that for changing the insertion depth adjustment the user has to exert deliberately onto the adjustment lugs 25 of the housing 3 a pre-set force directed radially in relation to the axis of the needle 11 to achieve, in turn, in the vicinity of the catches 16, a certain pre-determined force being able to deform the housing 3 and to displace the catches 16 radially from the axis of the needle 11. Owing to this, the locating of the chosen adjustment of the insertion depth is reliable and any accidental change of the adjustment is not possible. With such a configuration, the positioning teeth 15 and the catches 16 function properly as the adjustment means of insertion depth in INSERTION DEPTH ADJUSTMENT PHASE and, at the same time, function properly as the locating means of insertion depth, respectively, first 15 and second 16, in Phases 1, 3, 4, 5 and 6 of the operation and functioning of the device, including especially Phases such as INSERTION PHASE, INJECTION or TAKING PHASE, RETRACTION PHASE of the needle 11 from the patient's body and LOCKING PHASE of the device. In the presented embodiment of the safety needle device of the variant with the insertion depth adjustment, the longitudinal adjustment of the insertion depth and the longitudinal locating of the insertion depth adjustment have been provided.

In this phase, before the start of the insertion, the distal end 13 of the needle 11 is, independently of the chosen insertion depth, permanently visible in the viewing opening 21 in the protecting shield 4, FIGS. 7, 9-14. To take advantage of this, the user checks the state of the needle 11, that is its appearance and patency, and vents the needle 11.

The user inspects also whether the outer injection device has the proper pre-determined dose of the cosmetic and/or pharmaceutical composition adjusted for administration, and, if need be, corrects it.

Phase 3—Insertion, FIGS. 14-18

The user applies the distal end 5 of the protecting shield 4 to a place on the patient's body suitable for the intended insertion and presses the housing 3 of the device home in the direction towards the body.

Figure 15:
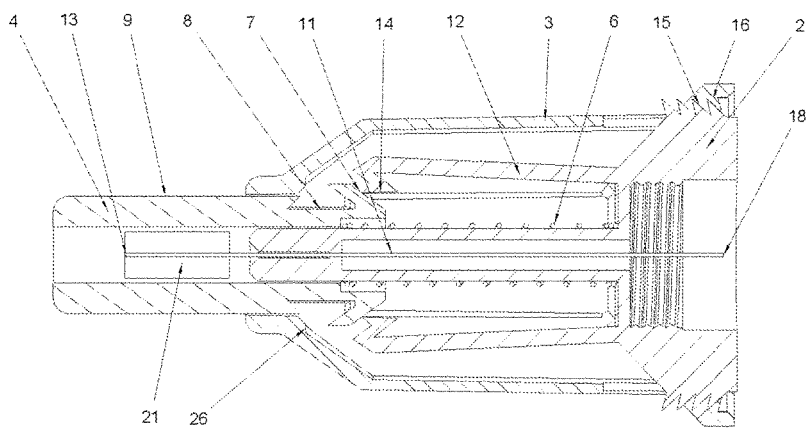
FIG. 15 shows a longitudinal cross-sectional view of the safety needle device of FIG. 1, at the beginning of INSERTION PHASE after triggers 7 have come into contact with catch pawls 14.

The protecting shield 4 begins to move longitudinally in the proximal direction deep into the housing 3 that is it moves relative to the hub 2 and to the housing 3, and the spring 6 is being compressed, FIG. 15. In the course of the movement of the protecting shield 4, the triggers 7 contact the respective catch pawls 14 on the elastic arms 12, FIG. 15, draw them together with the elastic arms 12 aside from the longitudinal axis of the needle 11 in the perpendicular direction, FIGS. 15-16, and, next, move over and beyond the catch pawls 14 in the proximal direction, that is in the direction towards the proximal end 18 of the needle 11 from the side of the medical instrument, FIG. 16. Simultaneously, the catch pawls 14 slip off the triggers 7 over the locking openings 8 onto the respective guides 9 of the protecting shield 4, see FIG. 17. In this moment of the functioning of the device, the protecting shield 4 crossed a "locking point", in which a "release" or an "actuation" of the blocking of the device against re-use takes place. When the "locking point" is crossed by the protecting shield 4, then the catch pawls 14 slide onto the guides 9 and the distal end 13 of the needle 11 brings into contact with the patient's body, see FIG. 17. After crossing the "locking point", the protecting shield 4 moves further in the proximal direction relative to the hub 2 and to the housing 3 until it is fully hidden inside the housing 3, as shown in FIG. 18. The distal surface 3a of the housing 3 and the distal surface 5a of the distal end 5 of the protecting shield 4 abut against the patient's body, wherein the distal surface 3a and the distal surface 5a are even with each other. The protecting shield 4 is in its extreme pressed position, which position corresponds to the performed full adjusted insertion depth. In the extreme pressed position of the protecting shield 4, the spring 6 is in the state of the maximal compression inside the device. The extreme pressed position of the protecting shield 4 is a transitional, unstable, position of the protecting shield 4 during use of the device.

Figure 17:
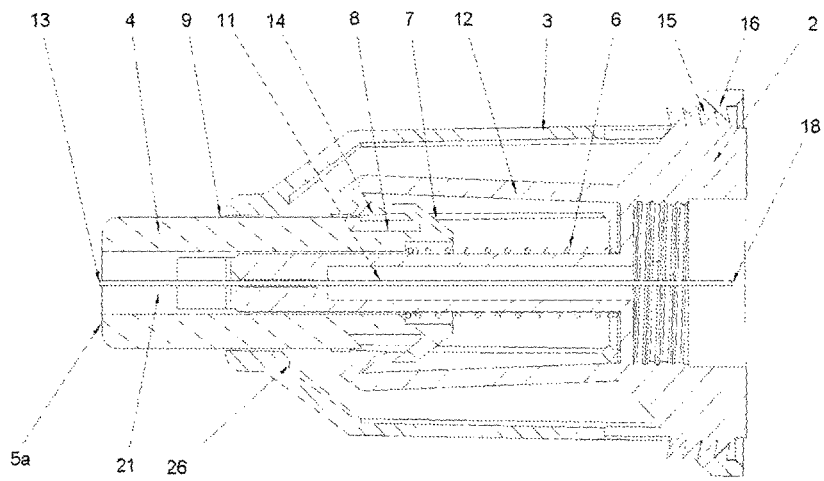
FIG. 17 shows a longitudinal cross-sectional view of the safety needle device of FIG. 2, in INSERTION PHASE at the moment when a distal end 13 of the needle 11 from the patient's side is being commenced to be inserted into the patient's body.
Figure 18:
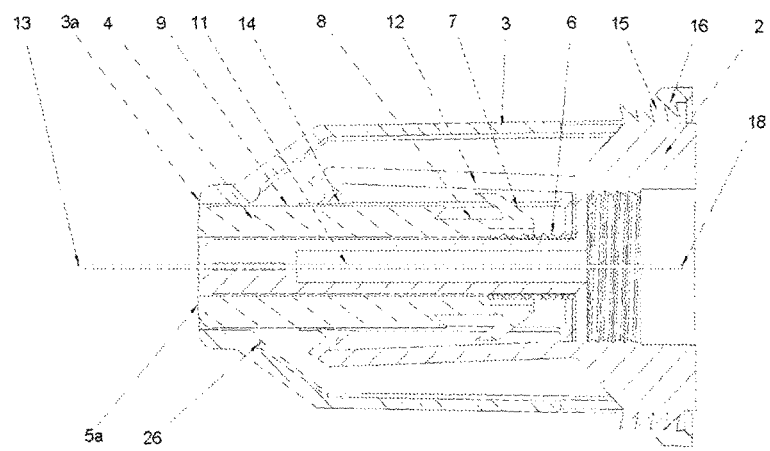
FIG. 18 shows a longitudinal cross-sectional view of the safety needle device of FIG. 2, in INSERTION PHASE with the protecting shield 4 in its extreme pressed position relative to the hub 2 and to the housing 3, which position corresponds to an adjusted and performed full insertion depth.

The safety needle device according to the present invention has such a construction that the blocking of the device against re-use is irreversibly actuated in the moment when the protecting shield 4 crosses the "locking point" during its movement in the proximal direction deep into the housing 3, after pushing the protecting shield 4 to the patient's body, as shown in FIG. 17. The blocking of the device against re-use is actuated already at a minimal coming out of the distal end 13 of the needle 11 outside and beyond the distal surface 5a of the distal end 5 of the protecting shield 4 in the course of the movement of the protecting shield 4 in the proximal direction. This means that in the moment of contacting the distal end 13 of the needle 11 with the patient's body, the blocking of the device against its re-use is already activated or launched out although the locking means against re-use of the device, that is the triggers 7 and the locking openings 8 on the protecting shield 4 and the catch pawls 14 on the elastic arms 12, are not mutually interlocked with each other yet. After crossing by the protecting shield 4 the "locking point", the safety needle device is not able to return to the pre-use state and is locked against re-use although it is not used yet. The insertion of the distal end 13 of the needle 11 can take place only once. Thus, the reliable locking of the device against re-use is being performed in the course of the first use of the device, because the locking means against re-use of the device, that is the triggers 7 and the locking openings 8 on the protecting shield 4 and the catch pawls 14 on the elastic arms 12, and the spring 6 cooperating with them, are configured so that during the first use of the device they block the movement of the elastic arms 12 in the direction perpendicular from the axis of the needle 11. In the present safety needle device, there is no possibility of accidental or unintentional puncture or injury with the needle neither prior to use nor after use of the device.

Figure 16:
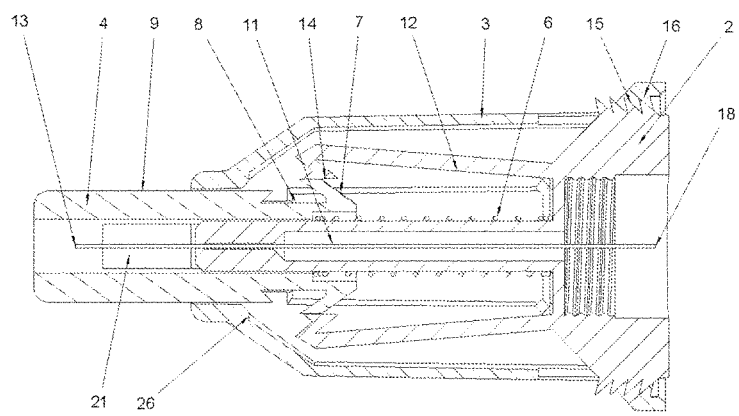
FIG. 16 shows a longitudinal cross-sectional view of the safety needle device of FIG. 2, in INSERTION PHASE at the moment when the catch pawls 14 are being moved away from an axis of the needle 11 by the triggers 7.

Additionally, the important thing is that the elastic arms 12 are being put under tension in the course of use of the device only, and precisely at the beginning of INSERTION PHASE during the movement of the protecting shield 4 deep into the housing 3, when the triggers 7 contact the catch pawls 14 of the elastic arms 12 and draw them together with the elastic arms 12 aside in the direction perpendicular from the longitudinal axis of the needle 11, FIGS. 15-16. As a result of this, the elastic characteristics of the elastic arms 12 are maintained in time and their reliability in functioning is guaranteed.

In the present safety needle device, the protecting shield 4, which contacts the patient's body, during use of the device realizes longitudinal movements only. The safety and comfort of the patient in this issue results from the fact that a rotation of the protecting shield 4 while contacting the patient' skin, especially the skin hard or rough, could be difficult and could disturb or, even, stop the correct functioning of the device. Moreover, a friction of a component part of the device against the patient's body would be for him or for her a source of unpleasant sensations.

During use of the present device, in INSERTION PHASE and in RETRACTION and LOCKING PHASE, the protecting shield 4 is precisely guided directly inside the housing 3 and directly relative to the cooperating locking means against re-use of the device that is relative to the elastic arms 12 and to the catch pawls 14, without any transitional means, which is of significance for the reliability of the functioning of the blocking of the device against re-use.

The spring 6, in INSERTION PHASE and in RETRACTION and LOCKING PHASE, acts directly between the protecting shield 4 and the hub 2, without any direct influence onto the locking means against re-use of the device and thereby without any disadvantageous impact onto the effectiveness of the blocking.

Phase 4—Injection or Taking (not Presented in FIG.)

When the full adjusted insertion depth is obtained, FIG. 18, the user holds the device in an unchanged position relative to the body and makes the injection of the pre-set dose of the cosmetic and/or pharmaceutical composition or takes the tissue sample, by pushing a piston of the outer injection device home according to instructions of a producer of the device or, respectively, by pulling the piston out.

Phase 5—Retraction of the Needle 11 from the Patient's Body and Locking of the Device, FIGS. 19-20

When INSERTION PHASE and INJECTION or TAKING PHASE are completed, the user moves the safety needle device away from the patient's body until the distal end 13 of the needle 11 is retracted outside from the body.

During the retraction of the needle 11 from the body, the protecting shield 4 is being automatically slid outside from the housing 3 such that a portion of the needle 11, which is being retracted, is being automatically progressively shielded until the complete taking the distal end 13 out from the body. In consequence, the needle 11 and the distal end 13 are constantly shielded, respectively, by the body and by the protecting shield 4 sliding out of the housing 3. This is caused by the spring 6, which when released from the load of the protecting shield 4 moved away of the patient's body after making the injection or performing the taking, begins to decompress automatically from its state of the maximum compression in the device in Phase 4, that is in INJECTION or TAKING PHASE, and pushes the protecting shield 4 in the distal direction outside the housing 3. The spring 6, while decompressing, moves the protecting shield 4 relative to the hub 2 and to the housing 3 in the direction of the distal end 13 of the needle 11, and beyond the distal end 13 till the position of the extreme moving out of the protecting shield 4 relative to the hub 2 and to the housing 3 after use of the device, which position corresponds to the final position of the protecting shield 4 relative to the hub 2 and to the housing 3 and in which position the device is locked such that it cannot be re-used.

While moving the protecting shield 4 out in the distal direction during Phase 5, that is during RETRACTION and LOCKING PHASE, the catch pawls 14 are being guided onto the guides 9 until they engage the locking openings 8 and the triggers 7, FIG. 19.

After completion of this operation phase of the device, the protecting shield 4 is in its final position relative to the hub 2 and to the housing 3 that is in such a position in which the distal end 13 of the needle 11 is completely shielded, which is safe for the user.

FIG. 19 shows the device in the locked after-use state, with the locking means of the device against re-use coupling mutually with each other. To engage the locking means against re-use of the device fixedly and irreversibly, the triggers 7 and the locking openings 8 on the protecting shield 4 as well as the catch pawls 14 on the elastic arms 12, including the elastic arms 12 as themselves, are specifically configured.

The elastic arms 12 extend longitudinally from the hub 2. The longitudinal dimension of the elastic arms 12 is measured along the axis of the needle 11 and is an axial dimension in the device, and constitutes the length of the elastic arms 12. The length of the elastic arms 12 is configured such that, on one hand, they are as long as possible, to provide them with a high resilience necessary to draw them aside from the axis of the needle 11 during INSERTION PHASE and, then, necessary to jam the catch pawls 14 reliably inside the locking openings 8 in RETRACTION and LOCKING PHASE, as well as to contact the catch pawls 14 as quickly as possible with the oblique proximal surface of the triggers 7 and to cross by the protecting shield 4 as quickly as possible the "locking point", which actuates the blocking in INSERTION PHASE when the distal end 13 starts to move out from the protecting shield 4. However, on the other hand, the length of the elastic arms 12 is configured such that before beginning of INSERTION PHASE and with the adjustment of the biggest insertion depth, to remain the catch pawls 14 with a small clearance y relative to the oblique proximal surface of the triggers 7 that is to remain the elastic arms 12 unbiased before beginning of INSERTION PHASE. The clearance y is the distance between the catch pawls 14 and the oblique proximal surface of the triggers 7, the distance which is measured along the axis of the needle 11. The pre-set clearance y, preferably, is from about 0.25 mm to about 0.50 mm, at the travelling of the insertion depth adjustment equals to 1 mm. This means that the elastic arms 12 have such a length that, at the adjustment of the smallest insertion depth, the distance between the catch pawls 14 and the oblique proximal surface of the triggers 7 is a1-a5+y, see FIG. 9, and that, at the adjustment of the second insertion depth being the first of the transitional insertion depths, the distance between the catch pawls 14 and the oblique proximal surface of the triggers 7 is a2-a5+y, see FIG. 12, and that, at the adjustment of the biggest insertion depth, the distance between the catch pawls 14 and the oblique proximal surface of the triggers 7 is a5-a5+y, see FIG. 13.

As shown in FIG. 20, the catch pawls 14 on the elastic arms 12 are configured with the distal detent 14a and the proximal detent 14b and with the distal undercut 14c and the proximal undercut 14d. The locking opening 8 of the protecting shield 4 is configured with the distal undercut 8a and the proximal undercut 8b as well as with the detent 8c. The trigger 7 of the protecting shield 4 is configured with the detent 7a. The trigger 7 has also the oblique proximal surface to guide the distal detent 14a of the catch pawl 14 at the beginning of INSERTION PHASE.

In the final position of the protecting shield 4, shown in FIGS. 19 and 20, the distal end 13 is exactly in the distance b with the clearance c from the distal surface 5a of the distal end 5 of the protecting shield 4, that is in the distance from the range of (b, b-c), wherein c is the range of the possible movement of the protecting shield 4 along the axis of the needle 11 after use of the device, in its final position, in the proximal direction against the spring 6 or in the distal direction under action of the spring 6. At the same time, c is a smaller one of the two distances, namely the distance between the detent 8c and the distal undercut 14c or the distance between the distal undercut 8a and the distal detent 14a.

To guarantee, complete and safe to the user, shielding of the distal end 13 of the needle 11 by the protecting shield 4 after use of the device, that is in the final position shown in FIG. 19, the relationship between the discussed above distances is a1, a2, . . . a5>b>c, wherein the minimal value of b is configured so that b=c+pre-set 4-5 mm. Then, the distal end 13 of the needle 11 remains inside the protecting shield 4 and any contact between the distal end 13 and the user is precluded.

Simultaneously, with relation to FIG. 20, for the proper functioning of the device, the longitudinal dimension d of the surface the catch pawl 14, that is the surface facing the direction towards the axis of the needle 11, is greater than the distance e, that is d>e, in order to force the catch pawl 14 at the beginning of INSERTION PHASE to "fall" or to "slip" with its surface of longitudinal dimension d down onto the guide 9 of the protecting shield 4. Furthermore, longitudinal dimension f of the locking opening 8 at the level of the detent 8c is greater than longitudinal dimension d, that is f>d, in order to force the catch pawl 14 in RETRACTION and LOCKING PHASE to "fall" with its surface of longitudinal dimension d into the locking opening 8 in the protecting shield 4. Wherein, d is the longitudinal dimension of the surface of the catch pawl 14, essentially corresponding to the distance between the distal detent 14a and the proximal detent 14b, e is the distance between the detent 8c and the detent 7a along line parallel to the axis of the needle 11, and f is the longitudinal dimension, that is along line parallel to the axis of the needle 11, of the locking opening 8 at the level of the detent 8c.

With such a precise configuration of the locking means against re-use of the device, cooperating with the spring 6, after single-use of the device, the second drawing aside the elastic arms 12 in the direction perpendicular to the axis of the needle 11 is precluded, and the protecting shield 4 is locked in the distal direction and in the proximal direction along the axis of the needle 11. In the distal direction, when the protecting shield 4 is pushed out by the spring 6, owing to the engagement of the detent 7a, the proximal undercut 14d, the proximal undercut 8b, the proximal detent 14b and the elastic arm 12. In the proximal direction, when the protecting shield 4 is pushed deep into the housing 3 under the external force applied against the action of the spring 6, owing to the engagement of the detent 8c, the distal undercut 14c, the distal undercut 8a, the distal detent 14b and the elastic arm 12.

Thanks to the earlier irreversible actuation of the blocking of the device against re-use, that is at the very beginning of INSERTION PHASE, the protecting shield 4, after completion of RETRACTION PHASE of the needle 11 from the patient's body and LOCKING PHASE of the device, is reliably locked in its final position.

In this phase, in the after-use state of the device, with the protecting shield 4 in the final position, the spring 6 and the elastic arms 12 are biased.

After locking the device, the indicator 23 on the protecting shield 4 is visible in the opening 20 in the housing 3, FIGS. 4, 8.

Phase 6—Removal and Securing, FIG. 8

The safety needle device after use, as shown in FIG. 8, is disassembled from the outer medical instrument by unscrewing the hub 2 from the outer medical instrument, and is disposed with its end from the side of the medical instrument inside the outer casing 1, FIG. 1, for the purpose of safety utilization according to the instruction of the manufacturer of the device. The proximal end 18 of the needle 11 is placed inside the outer casing 1.

The Safety Needle Device in the Variant with the Fixed Insertion Depth

The safety needle device, in an embodiment of the variant with the fixed insertion depth, is shown in FIGS. 1A-14A and FIG. 20.

The construction of the safety needle device with the fixed insertion depth has been designed to provide the user of devices of this type with a device with only one determined insertion depth, already corresponding to the desired insertion depth, without any necessity to adjust the insertion depth, which in some circumstances or in case of some patients is too troublesome or dangerous.

As shown in FIGS. 1A-3A, on the whole, the safety needle device in the variant with the fixed insertion depth is constructed from the same component parts as the device in the variant with the insertion depth adjustment, that is from a hub 2, a needle 11, a protecting shield 4, longitudinal resilient means 6, transverse resilient means 12 and a housing 3, which are all together with situated thereon technical means arranged and configured respectively to cooperate mutually with each other in order to realize different technical functions of the device, respective for the variant with the fixed insertion depth. The presented herein embodiment of the safety needle device in the variant with the fixed insertion depth, comprises as longitudinal resilient means 6 the spring 6 and as transverse resilient means 12 two elastic arms 12. The elastic arms 12 are made from plastic as a single continuous part together with the hub 2 in the technological process of injection moulding, and constitute a single assembly part of the device as shown in FIGS. 1A-14A.

The structure and the functioning principle of the safety needle device in the variant with the fixed insertion depth are generally very similar to the safety needle device in the variant with the insertion depth adjustment. The differences in the structure and in the functioning principle consist in and are related to the fact that, in the variant with the fixed insertion depth, the device is devoid of adjustment means adjusting the insertion depth and indication means of insertion depth adjustment.

For indication of the determined insertion depth, the device is provided with information means of insertion depth disposed on the housing 3, for example, with the insertion depth of 4 mm, as shown in FIG. 2A. However, the insertion depth may also be indicated, for example, on a distal end 5 of the protecting shield 4.

For reliable and fixed locating of a position of the housing 3 relative to the hub 2, locating means of insertion depth, first 15 and second 16, are respectively configured.

Remaining technical means performing different functions of the device in the variant with the fixed insertion depth are the same, namely, retaining means for retaining said protecting shield in an initial position, locking means against re-use of said device, guiding means of said locking means against re-use of said device and indication means of the state of use of said device.

For the sake of simplicity and clarity, the below description of the preferred embodiment of the safety needle device in the variant with the fixed insertion depth, will not repeat all the device features that are identical to both variants, including activities of the operation and functioning phases, that is the features presented and explained during the presentation of the operation and functioning phases of the device. The features of the variant with the fixed insertion depth, which distinguish this variant from the variant with the insertion depth adjustment, will be herein indicated and described. Therefore, the following description of the safety needle device in the variant with the fixed insertion depth should be understood as encompassing the description of the features common for both variants. At the same time, due to the detailed description of the device embodiments in both variants and the drawings, it will be clear for a person skilled in art which features of both variants are common and which differentiate the variants from each other.

Figure 5A:
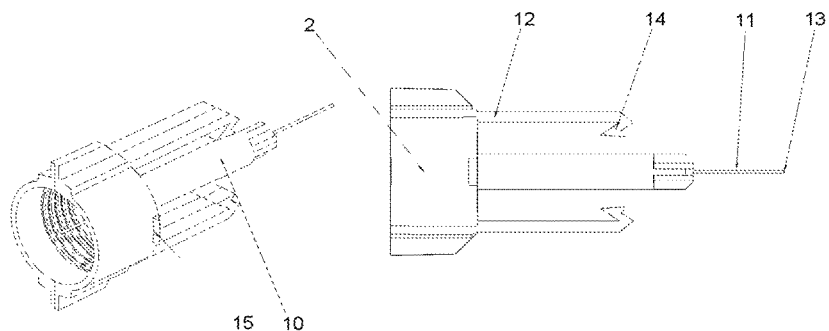
FIG. 5A shows perspective and side views of a hub 2 with elastic arms 12, a positioning tooth 15, a needle 11 of the safety needle device of FIG. 2A.
Figure 6A:
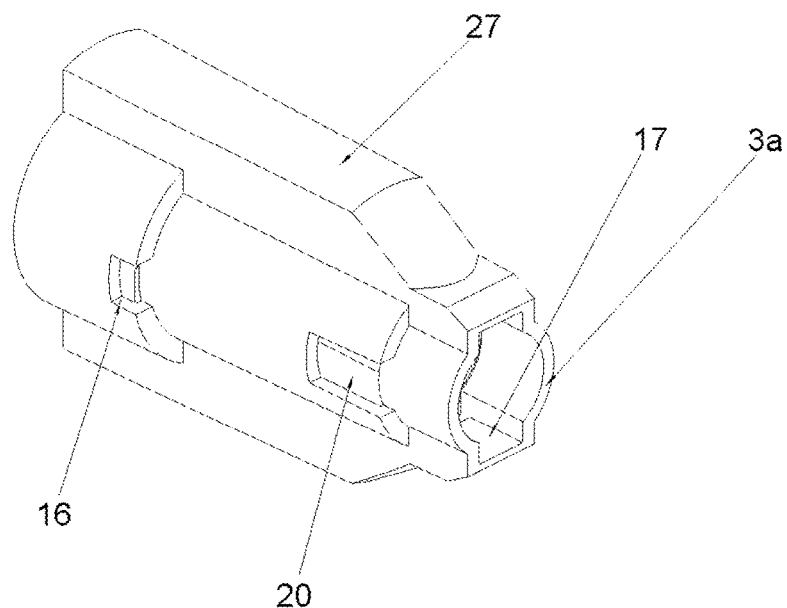
FIG. 6A shows a perspective view of a housing 3 of the device of FIG. 2A.

The housing 3, in the variant of the device with the fixed insertion depth, is immovably mounted onto the hub 2, wherein its position relative to the hub is fixedly located by the first locating means of insertion depth 15 on the hub 2, as clearly shown in FIG. 5A, and by the second locating insertion depth means 16 on said housing 3, as clearly shown in FIG. 6A, the means being fixedly engaged with each other. In the presented embodiment of the device in the variant with the fixed insertion depth, the first locating means of insertion depth 15 is in the form of two positioning teeth 15 being arranged circumferentially and opposite to each other, and the second locating means of insertion depth 16 is in the form of two apertures 16 being arranged circumferentially and opposite to each other. The positioning teeth 15 of the hub 2 are snapped in the apertures 16 of the housing 3 thanks to the elasticity of the housing 3. However, the position of the housing 3 may be fixedly set relative to the hub 2 by other known technical means including techniques such as interference fit, gluing or joining by heat treatment. In the safety needle device in the variant with the fixed insertion depth, the housing 3 has a precisely determined position relative to the hub 2 along the axis of the needle 11, which corresponds to the determined insertion depth, for example 4 mm, as clearly shown in FIGS. 2A, 7A-8A.

OPERATION and FUNCTIONING PHASES of the Device in the Variant with the Fixed Insertion Depth Phase 1—Preparation of the Safety Needle Device for Use, FIGS. 1A-2A, 7A, 9A In case of the safety needle device in the variant with the fixed insertion depth, the user begins with a choice of a safety needle device with the fixed insertion depth that is suitable for him or her. The insertion depth, a fixed one in this variant of the device, is indicated on a protection packaging of the device (not presented in Figs.).

Figure 9A:
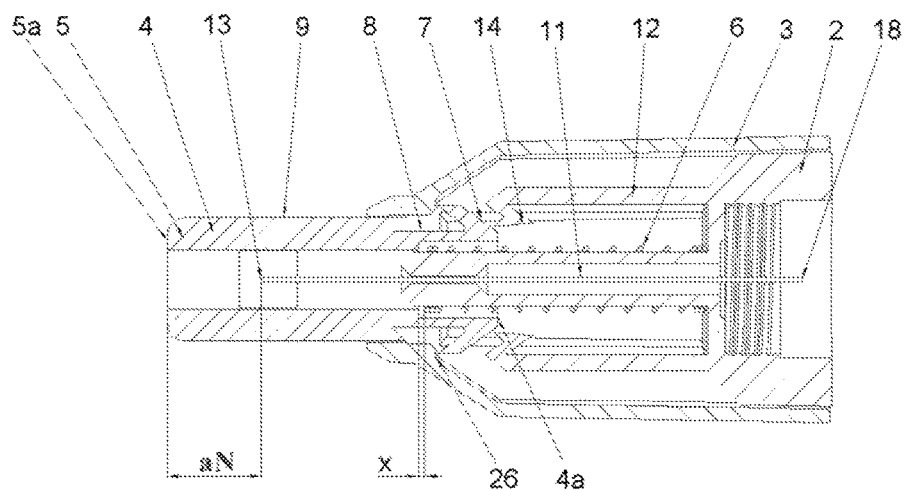
FIG. 9A shows a longitudinal cross-sectional view of the safety needle device of FIG. 2A, before use, with a spring 6 unbiased, and with the protecting shield 4 in its initial position.
Figure 9:
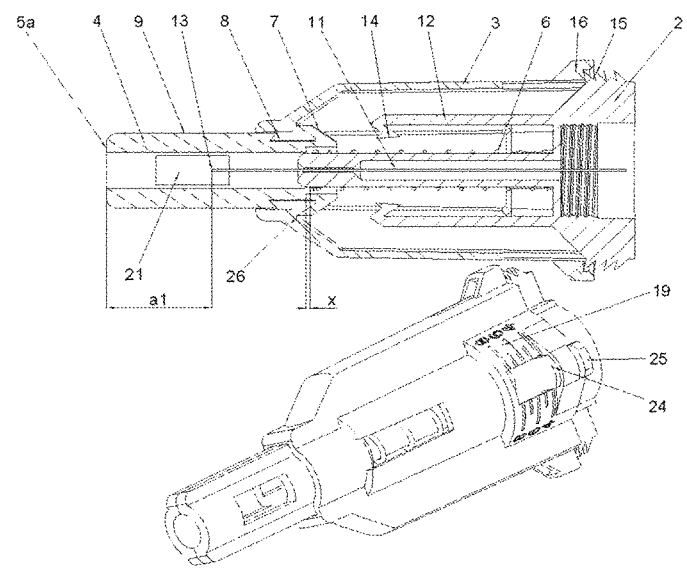
FIG. 9 shows perspective and longitudinal cross-sectional views of the safety needle device of FIG. 2, before use, with an initial adjustment of the smallest insertion depth, with a spring 6 unbiased, and with the protecting shield 4 in an initial position.

The device is delivered to the user with the determined insertion depth, wherein the length of the spring 6 is matched respectively to this fixed determined insertion depth, that is the length of the spring 6 is matched in such a manner that prior to the use of the device, the spring 6 is not pre-biased, as shown in FIG. 9A. The spring 6 is not put under tension until Phase 3, that is during INSERTION PHASE. The spring 6 remains biased after the use of the device.

In this phase, in a pre-use state of the device, with the protecting shield 4 in its initial position, apart from the spring 6, also elastic arms 12 are unbiased, FIG. 9A.

The lack of tension of the spring 6 and the elastic arms 12 in the pre-use state of the device is advantageous for a secure exploitation of the device as described above in respect to the variant of the device with the insertion depth adjustment.

At the same time, similarly to the safety needle device in the variant with the insertion depth adjustment with the protecting shield 4 in the initial position, the protecting shield 4 has a small pre-set range of a longitudinal travelling x, which is preferably from about 0.25 mm to about 0.50 mm. Wherein herein, that is in the safety needle device in the variant with the fixed insertion depth, x is the smaller distance of the two following distances, namely, of the distance between the spring 6 and the protecting shield 4, and, precisely, between a distal end of the spring 6 and a bottom of a chamber receiving the spring 6 inside the protecting shield 4, or of the distance between the trigger 7 of the protecting shield 4 and a catch pawl 14 of the elastic arm 12, and precisely, between an oblique proximal surface of the trigger 7 of the protecting shield 4 and a detent 14a of the catch pawls 14 of the elastic arm 12, as shown in FIG. 9A.

In the safety needle device in the variant with the fixed insertion depth, before the use of the device the protecting shield 4 is in its initial position, in which a distal end 13 of the needle 11 is from a distal surface 5a of the distal end 5 of the protecting shield 4 within a distance aN with a clearance x, that is within the distance of a range (a1, a1-x), wherein N is a number of determined insertion depths, and is equal to, for example, 5, that is N=5, in the case when the device in the variant with the fixed insertion depth is mounted with five possible fixed determined insertion depths, as shown in FIG. 9A.

Phase 1 that is PREPARATION PHASE of the device, in the variant with the fixed insertion depth, besides the first action of choosing the device right away with the determined insertion depth desired by the patient, is identical to Phase 1 for the device in the variant with the insertion depth adjustment.

Figure 7A:
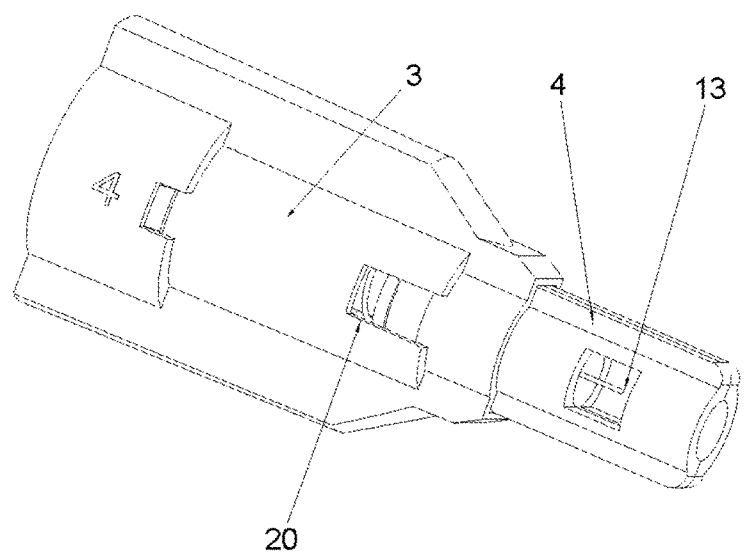
FIG. 7A shows a perspective view of the safety needle device of FIG. 2A, before use, with an indicator 23 of the state of use of the device invisible in an opening 20.

Phase 2—Checking an Insertion Depth Adjustment, FIGS. 2A, 7A-9A and, in case of an outer medical instrument in the form of an injection device, checking the adjustment of an injected dose or the choice of the injection device with a proper dose of the cosmetic and/or pharmaceutical composition for administration The user, on the housing 3 of the device taken out of an outer casing 1, verifies whether the device has the required insertion depth, which corresponds to his or her needs. The insertion depth, fixed in this variant of the device, is indicated not only on the protective packaging of the device but also on the housing 3, as shown in FIG. 2A, 7A.

In the presented embodiment of the safety needle device in the variant with the fixed insertion depth, the positioning teeth 15 on the hub 2 and the apertures 16 on the housing 3 are configured so that the location of the position of the housing 3 relative to the hub 2 and the fixing of the determined insertion depth are reliable.

Phase 3—Insertion, FIGS. 9A-13A

Phase 3 that is INSERTION PHASE for the device in the variant with the fixed insertion depth, is identical to Phase 3 that is INSERTION PHASE for the device in the variant with the insertion depth adjustment.

Wherein, in case of the variant of the device with the fixed insertion depth, the extreme pressed position of the protecting shield 4 deep into the housing 3 and into the hub 2 corresponds to the performed full determined insertion depth.

Phase 4—Injection or Taking (not Shown in FIG.)

Phase 4 that is INJECTION or TAKING PHASE for the device in the variant with the fixed insertion depth is identical to Phase 4, that is to INJECTION or TAKING PHASE for the device in the variant with the insertion depth adjustment.

Figure 8A:
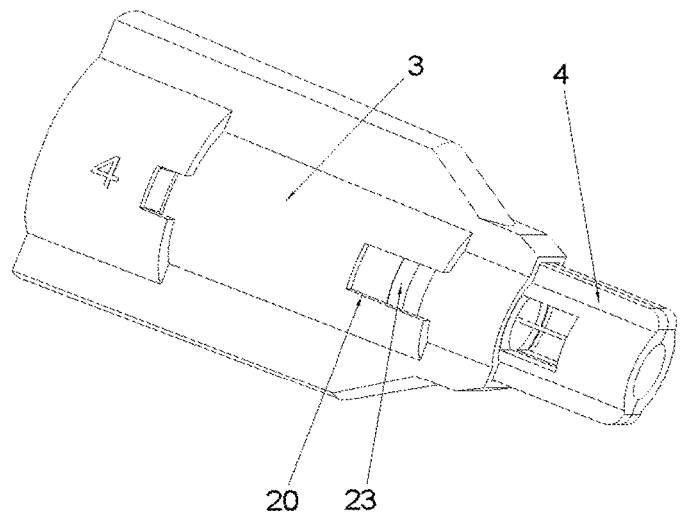
FIG. 8A shows a perspective view of the safety needle device of FIG. 2A, after use, with the indicator 23 of the state of use of the device visible in the opening 20.

Phase 5—Retraction of the Needle 11 from the Patient's Body and Locking of the Device, FIGS. 8A, 14A

With relation to the described above, in case of the safety needle device in the variant with the insertion depth adjustment, issue of the length of the elastic arms 12, that is their longitudinal dimension, also in this variant of the device with the fixed insertion depth the elastic arms 12 have such a length so that at the fixed position of the housing 3 relative to the hub 2, located during an assembly of the device, the position corresponding to the fixed determined insertion depth chosen from the available insertion depths, the distance between the catch pawls 14 and the oblique proximal surface of the trigger 7 is aN-a5+y, see FIG. 9A, wherein N is equal to, for example, 5, that is N=5, in the case when the device in the variant with the fixed insertion depth is mounted with five possible fixed determined insertion depths.

Configuration of the catch pawls 14 on the elastic arms 12 and locking openings 8 and triggers 7 on the protecting shield 4 has been explicitly shown in FIG. 20, where they are presented after their mutual engagement with each other, after locking the device against a re-use when the protecting shield 4 is in the final position, which FIG. 20 is common for both variants of the device.

In the final position of the protecting shield 4, shown in FIG. 19A and FIG. 20, in the same way as in the variant of the device with the insertion depth adjustment, the distal end 13 of the needle 11 is exactly within the distance b with the clearance c from the distal surface 5a of the distal end 5 of the protecting shield 4, that is the distance is within the range (b, b-c), wherein c is the range of a possible movement of the protecting shield 4 along the axis of the needle 11 after the use of the device. Similarly, the dependence between the distances described is aN>b>c, wherein the minimal value of b is designed so that b=c+pre-set 4-5 mm.

And further, similarly, with relation to FIG. 20, relationships between the distances described d, e, f are such that dimension d is greater than distance e, that is d>e, and dimension f is greater than dimension d, that is f>d.

In this phase, in the after-use state of the device, with the protecting shield 4 in the final position, the spring 6 and the elastic arms 12 are biased.

After locking the device, an indicator 23 on the protecting shield 4 is visible in openings in the housing 3, FIG. 7A, 8A.

Phase 5, that is RETRACTION and LOCKING PHASE, for the device in the variant with the fixed insertion depth, is identical to Phase 5, that is RETRACTION and LOCKING PHASE, for the device in the variant with the insertion depth adjustment.

Phase 6—Removal and Securing, FIGS. 8A and 14A

Phase 6, that is REMOVAL and SECURING PHASE, for the device in the variant with the fixed insertion depth, is identical to Phase 6, that is REMOVAL and SECURING PHASE, for the device with the variant with the insertion depth adjustment.

Among remarks concerning the overall construction of the present safety needle device in both variants, that is with the insertion depth adjustment and with the fixed insertion depth, it should be noted that the protecting shield 4, which contacts the patient's body, performs during use of the device only longitudinal movements. Safety and comfort of the patient in this matter results from the fact that the rotation of the protecting shield 4 while contacting the patient's skin, especially a hard or rough skin, could be hindered and could disturb and even impede the correct functioning of the device. Moreover, friction between the component part of the device and the patient's body would also be for the patient a source of unpleasant impressions.

Other movable component parts of the safety needle device also realize only longitudinal or transversal movements relative to the axis of the needle 11 in any of OPERATION and FUNCTIONING PHASES of the device.

The lack of any rotational movements relative to the axis of the needle 11 of any component parts of the device, which would be necessary for the user to perform in order to prepare the device for use or which would be independent of the user and related to functioning of the device, simplify the structure and functioning as well as operation of the device.

Furthermore, during the use of the present device, in INSERTION PHASE and in RETRACTION and LOCKING PHASE, the protecting shield 4 is precisely guided directly by the housing 3 and directly relative to the cooperating locking means against re-use of the device, that is relative to the elastic arms 12 and to the catch pawls 14, without any intermediate means, which is significant for reliability of the functioning of the blocking of the device against re-use.

Similarly, the spring 6, in INSERTION PHASE and in RETRACTION and LOCKING PHASE, acts directly between the protecting shield 4 and the hub 2, without any direct reaction onto the locking means against re-use of said device and thereby without disadvantageous influence onto the effectiveness of the blocking.

Advantages Of The Invention

The advantage of the present invention is that the needle end from the patient's side is shielded, safely for the users, both prior to the primary use of the device, and permanently and securely after a single use of the device, wherein the shield of this needle end activates automatically, immediately after being taken out from the patient's body, still before the removal of the entire device from the outer medical instrument.

Another advantage of the present device is that it has the construction precluding a re-use of the device after a single use thereof.

Another advantage of the invention is that it guarantees reliability of shielding the needle end from the patient's side after performing an insertion and an injection or after taking a body tissue, and after retracting the needle from the patient's body, and it guarantees a blocking of the device against a re-use, without disadvantageous enlargement of the size of the device and without increasing the number of its component parts.

The safety needle device according to the invention has the protecting shield for the needle, which is provided with the viewing opening designed in such a manner that it enables observation of the needle during the manufacture process of the device, thanks to which it is possible to control whether mounting of the needle in the hub is correct, for example, to control the coaxiality of the needle and the hub, and the entire device. The same viewing opening in the protecting shield, gives the user, that is a patient or a nurse, an opportunity to examine the needle distal end from the patient's side prior to the use of the device in order to check the state of the needle, that is whether the needle is straight and patent, as well as it gives the user an opportunity to observe the needle during its preparation for insertion. Preparation of the needle consists in expelling all air entrapped within the needle bore. The correct alinement of the needle in the hub and in the entire device as well as a correct vent of the needle prior to the use of the device has a crucial significance for the patient's safety. Simultaneously, the inspection of the needle during INSERTION PHASE, INJECTION or TAKING PHASE, RETRACTION PHASE of the needle, and during REMOVAL and SECURITY PHASE, in the present device, is hindered because during these phases, the needle with its distal end from the patient's side is situated in the patient's body and/or is shielded.

The important advantage of the safety needle device according the present invention is that none of the component parts is pre-biased or loaded, including the locking means against re-use of the device, which is subject to deformation only during INSERTION PHASE of the device operation. Moreover, the spring, which pushes the protecting shield from the patient's body outside the device in RETRACTION PHASE of the needle, operates directly between the protecting shield and the hub, without any impact onto the locking means and thereby without any disadvantageous impact onto the effectiveness of the blocking. The lack of an intermediate component part eliminates an additional element in the chain of dimensions, which results in a better "control" of the product reliability.

Yet another important advantage of the invention is that its structure effectively prevents any intervention of the user aiming at destroying the locking means against re-use of the device or at changing the state of the blocking in order to re-use the device or use it repeatedly. In the present solution of the safety needle, the user has no access to the locking means against re-use of the device neither prior to the use of the device, during any of the operational phases nor after a single use of the device.

The structure of the device enables to perform the medicine injection with the needle inserted into the patient's body at any angle, including "the right angle", which is convenient for and preferred by the patients and/or medical personnel and which simultaneously guarantees the insertion depth as declared in the given device and required by an individual patient. At the same time, the structure of the device is such that during the insertion and retraction of the needle from the body and during the injection, the protecting shield 4 shielding the needle 11 at the distal side, receives the load originating from the contact with the body and the needle is unloaded and freely enters and exits the body. This is important for the correct insertion and injection and safe for the patient, especially in case of a device for applications requiring a thin needle, as for insulin subcutaneous injections or for cosmetic anti-wrinkle agents.

The advantage of the invention is that the movable component parts of the device in any operation and functioning phase of the device realize only longitudinal and/or transverse movements relative to the needle axis.

Another advantage of the device is that it is provided with the indicator of the use of the device, which is not situated on the locking means against re-use of the device and is not accessible for the user, which renders changing of the state of use of the device impossible.

The construction of the present safety needle device enables its manufacturing with a non-metal spring, which further reduces production costs and facilitates the utilization of the device used.

The safety needle device, according to the present invention, in the variant with the insertion depth adjustment enables the adjustment of the insertion depth and the correction of the adjustment in an easy, safe and reliable manner, and is further provided with the indication of the chosen insertion depth. Such a universal device enables adaptation of the insertion depth to the needs of an individual patient in a given moment, and eliminates the necessity to gather an entire portfolio of such products, differentiated on account of the insertion depth.

The advantage of an utmost importance of the variant of the safety needle device with the insertion depth adjustment, according to the present invention, is that the adjustment of the insertion depth is realized by a movement of the housing, only, perpendicular and longitudinal relative to the needle axis, and not by a rotational movement of the housing relative to the hub or by a rotational movement of any other component part of the device. The rotational movement is reserved for the adjustment of the volume of the medicine dose in the injection instrument, for example, in the pen form. The lack of a rotatable movement during the change of the insertion depth adjustment in the present device is important because it eliminates the possibility to confuse the insertion depth adjustment with the dose adjustment of the injected medicine, which results in an improvement of safety and exploitation comfort of the device. The approach towards the feature of the insertion depth control as applied in the present safety needle device in its variant with the insertion depth adjustment is completely different than the one in the known safety needle devices.

Manipulation in the course of INSERTION DEPTH ADJUSTMENT PHASE is held a long way from the needle tip which remains constantly shielded, which minimizes the likelihood of accidental pricking.

The structure of the present safety needle device provides a possibility of manufacturing many component parts of the device in the form of four, three, two or even a single continuous structure part made of a homogeneous material, which improves the reliability of the functioning of the device.

The safety needle device according to the present invention is cheap, simple and has a minimal number of component parts, and simultaneously fulfills the requirements presently raised for advanced safety needle devices. The structure of the device ensures an easy assembly, which further reduces manufacturing costs. Thanks to the above mentioned features, the present safety needle device combines high safety and comfort of the use. As a result, the described safety needle device, according to the invention, meets the safety and reliability demands made on advanced safety needles, is structurally simple, cheap and easy in manufacturing as well as user-and environmentally friendly.

The present solution of the safety needle for the insulin pen guarantees a reliable functioning of the device and thereby provides the patient with the high level of exploitation comfort of this safety needle, which is now required in the field of medical devices of mass production and designed for application by an individual patient.

LIST OF COMPONENT PARTS AND STRUCTURE ELEMENTS

1. Outer casing
2. Hub
3. Housing
3a. Distal surface
4. Protecting shield
4a. Proximal surface
5. Distal end (of the protecting shield 4)
5a. Distal surface of the distal end
6. Coil spring
7. Trigger
7a. Detent
8. Locking opening
8a. Distal undercut
8b. Proximal undercut
8c. Detent
9. Guide
10. Support
11. Needle
12. Elastic arm
13. Distal end (of the needle 11)
14. Catch pawl
14a. Distal detent
14b. Proximal detent
14c. Distal undercut
14d. Proximal undercut
15. Positioning tooth
16. Catch (in the variant of the device with the insertion depth adjustment) Aperture (in the variant of the device with the fixed insertion depth)
17. Guiding groove
18. Proximal end (of the needle 11)
19. Scale
20. Opening
21. Viewing opening
22. Opening
23. Indicator
24. Indication tongue
25. Adjustment lug
26. Abutment surface
27. Protrusion

The invention claimed is:

1. A safety needle device for connection with a medical instrument to insert a needle into a patient's body to a determined insertion depth for injection of a cosmetic and/or pharmaceutical composition or for taking a tissue sample, including a bodily fluid sample, comprising:

a hub with fixing means for fixing said device onto the medical instrument, a needle mounted in said hub and having a proximal end for engagement with the medical instrument and a distal end for insertion into the patient's body, a protecting shield movable longitudinally to an axis of said needle between an initial position in a pre-use state of said device and a final position in an after-use state of said device, in both states said distal end of said needle is protected, longitudinal resilient means disposed between said hub and said protecting shield and acting longitudinally to said axis of said needle, a housing movably mounted onto said hub and slidably carrying said protecting shield, and transverse resilient means disposed within said housing and acting transversely relative to said axis of said needle, the hub, the needle, the protecting shield, the longitudinal resilient means, the housing, and the transverse resilient means configured for cooperation with each other, retaining means disposed on said protecting shield, said housing, said transverse resilient means and on said longitudinal resilient means for retaining said protecting shield in said initial position, locking means against re-use of said device disposed on said protecting shield and on said transverse resilient means for locking said protecting shield in said final position, guiding means of said locking means against re-use of said device disposed on said protecting shield for guiding said locking means against re-use of said device during use of said device, indication means of state of use of said device disposed on said protecting shield and on said housing for indicating the state of use of said device, locating means of insertion depth, first and second, disposed, respectively, on said hub and on said housing for locating a position of said housing relative to said hub longitudinally to said axis of said needle, said position corresponding to said determined insertion depth, adjustment means of insertion depth, movable and immovable, disposed, respectively, on said housing and on said hub for changing said position of said housing relative to said hub longitudinally to said axis of said needle and for changing an adjustment of an insertion depth, indication means of insertion depth adjustment disposed on said housing and on said hub for indicating an adjustment of an insertion depth, wherein in order to assure that changing of the adjustment of the insertion depth is performed by displacing said movable adjustment means of insertion depth exclusively longitudinally and transversely relative to said axis of said needle, said housing is configured so that it is elastically deformable in direction perpendicular relative to said axis of said needle for changing said adjustment of said insertion depth.

2. A device according to claim 1, wherein said adjustment means of insertion depth is configured to adjust between a first insertion depth and a second insertion depth, wherein the first insertion depth is less than the second insertion depth.

3. A device according to claim 1, wherein said movable adjustment means of insertion depth comprises on said housing, arranged circumferentially and opposite to one another, two adjustment lugs, and arranged circumferentially with circumferential displacement by 90° relative to said two adjustment lugs, at least one catch, and comprises on said hub, disposed opposite to said catch, at least one set of, arranged longitudinally one after another, at least two positioning teeth.

4. A device according to claim 1, wherein said housing is during an assembly of the device fixedly attached to said hub by one or more of interference fit, gluing, and coupling by heat treatment, wherein a position of said housing relative to said hub corresponds to only one determined insertion depth.

5. A device according to claim 1, wherein said locating means of insertion depth, first and second, are configured so that a position of said housing relative to said hub is during an assembly of the device located fixedly, said position corresponding to only one said determined insertion depth.

6. A device according to claim 5, wherein said first locating means of insertion depth comprises at least one circumferentially arranged positioning tooth and said second locating means of insertion depth comprises at least one circumferentially arranged aperture.

7. A device according to claim 1, wherein said housing is disposed onto said hub between set positions within a set travelling range relative to said hub longitudinally to said axis of said needle, wherein said set positions correspond to said determined insertion depths and said set travelling range corresponds to a determined range of said insertion depth.

8. A device according to claim 1, wherein for insertion of said needle to said determined insertion depth, said protecting shield is moved in a proximal direction to a retracted pressed position relative to said hub and said housing, wherein blocking of said device against re-use is irreversibly actuated when said distal end of said needle moves out of a distal surface of a distal end of said protecting shield in the course of movement of said protecting shield in said proximal direction, and wherein for reliable locking of said protecting shield in said final position and for permanent locking of said device against re-use, said locking means against re-use of said device cooperating with said longitudinal resilient means is configured so that it locks a movement of said transverse resilient means in direction perpendicular to said axis of said needle after single use of said device, and locking means against re-use of said device is covered by said housing so that it is invisible and inaccessible for a user before, during and after use of said device.

9. A device according to claim 1, wherein said protecting shield between said initial position and said final position moves exclusively longitudinally relative to said axis of said needle.

10. A device according to claim 1, wherein in said initial position of said protecting shield in said pre-use state of said device, said longitudinal resilient means and said transverse resilient means are unbiased.

11. A device according to claim 1, wherein in said final position of said protecting shield in said after-use state of said device, said longitudinal resilient means and said transverse resilient means are biased.

12. A device according to claim 1, wherein for locking said protecting shield in said final position, said locking means against re-use of said device is displaced exclusively, respectively, longitudinally and transversely relative to said axis of said needle.

13. A device according to claim 1, wherein said first locating means of insertion depth comprises arranged circumferentially at least one set of arranged longitudinally one after another at least two positioning teeth and said second locating means of insertion depth comprises arranged circumferentially at least one catch.

14. A device according to claim 1, wherein said housing is configured so that said positioning teeth and said catch perform a function of, respectively, said first and said second locating means of insertion depth or a function of said adjustment means of insertion depth, depending on an operation phase of said device.

15. A device according to claim 1, wherein said indication means of insertion depth adjustment comprises a scale on said housing and an indication tongue on said hub.

16. A device according to claim 1, wherein said indication means of state of use of said device is configured so that it is observable and inaccessible for said user before, during and after use of said device.

17. A device according to claim 1, wherein a distance (a1, a2, . . . aN, wherein N is a number of said determined insertion depths) between said distal surface of said distal end of said protecting shield and said distal end of said needle, in said initial position of said protecting shield, is different from a distance (b) between said distal surface of said distal end of said protecting shield and said distal end of said needle, in said final position of said protecting shield, and preferably is bigger.

18. A device according to claim 1, wherein said hub and, said longitudinal resilient means or said transverse resilient means, or said hub and said longitudinal resilient means and said transverse resilient means, or said longitudinal resilient means and said protecting shield, or said hub and said longitudinal resilient means and said protecting shield, or all component parts mentioned in this claim are integrally formed during a technological process as a single continuous part.

19. A device according to claim 1, wherein said retaining means for retaining said protecting shield in said initial position comprises a detent of at least one trigger on said protecting shield, at least one abutment surface on said housing, a distal detent of at least one catch pawl on said transverse resilient means and said longitudinal resilient means.

20. A device according to claim 1, wherein said longitudinal resilient means comprises a coil spring.

21. A device according to claim 1, wherein said locking means against re-use of said device comprises at least one locking opening and at least one trigger on said protecting shield, and at least one catch pawl on said transverse resilient means, and guiding means of said locking means against re-use of said device comprises at least one trigger and at least one guide on said protecting shield.

22. A device according to claim 1, wherein said transverse resilient means is attached to at least one component part chosen from a group comprising said hub, said housing and said needle.

23. A device according to claim 22, wherein said transverse resilient means comprises at least one elastic arm.

24. A device according to claim 1, wherein said indication means of state of use of said device comprises at least one indicator on said protecting shield and at least one opening on said housing.

25. A device according to claim 1, wherein for inspection of said needle during the manufacture process of said device and for control of patency and vent of said needle before the use of said device, said protecting shield is provided with a respectively configured viewing opening.

26. A device according to claim 1, wherein said device has an outer casing housing said device before its use and receiving said device after its use in order to guarantee to a user safe operation and utilization.

27. A safety needle device, for connection with a medical instrument to insert a needle into a patient's body to a determined insertion depth for injection of a cosmetic and/or pharmaceutical composition or for taking a tissue sample, including a bodily fluid sample, comprising:
   a hub with fixing means for fixing said device onto the medical instrument,
   a needle mounted in said hub and having a proximal end for engagement with the medical instrument and a distal end for insertion into the patient's body,
   a protecting shield movable exclusively longitudinally to an axis of said needle between an initial position in a pre-use state of said device and a final position in an after-use state of said device, in both states said distal end of said needle is protected,
   longitudinal resilient means disposed between said hub and said protecting shield and acting longitudinally to said axis of said needle between said initial position of said protecting shield, in which said initial position said longitudinal resilient means is unbiased, and said final position of said protecting shield, in which said final position said longitudinal resilient means is biased,
   a housing immovably mounted onto said hub and slidably carrying said protecting shield, and
   transverse resilient means disposed within said housing and acting transversely relative to said axis of said needle, said transverse resilient means in said initial position of said protecting shield being unbiased and in said final position of said protecting shield being biased,
   the hub, the needle, the protecting shield, the longitudinal resilient means, the housing, and the transverse resilient means configured for cooperation with each other,
   retaining means disposed on said protecting shield, said housing, said transverse resilient means and on said longitudinal resilient means for retaining said protecting shield in said initial position,
   locking means against re-use of said device disposed on said protecting shield and on said transverse resilient means and movable exclusively, respectively, longitudinally and transversely relative to said axis of said needle for locking said protecting shield in said final position,
   guiding means of said locking means against re-use of said device disposed on said protecting shield for guiding said locking means against re-use of said device during use of said device,
   indication means of state of use of said device disposed on said protecting shield and on said housing, being observable and inaccessible for a user before, during and after use of said device, for indicating the state of use of said device,
   wherein for insertion of said needle to said determined insertion depth, said protecting shield is moved in a proximal direction to an extreme pressed position relative to said hub and said housing,
   wherein blocking of said device against re-use is irreversibly actuated when said distal end of said needle moves out of a distal surface of a distal end of said protecting shield in the course of movement of said protecting shield in said proximal direction, and
   wherein for reliable locking of said protecting shield in said final position and for permanent locking of said device against re-use, said locking means against re-use of said device cooperating with said longitudinal resilient means is configured so that it locks a movement of said transverse resilient means in direction perpendicular to said axis of said needle after single use of said device, and said locking means against re-use of said device is covered by said housing so that it is invisible and inaccessible for a user before, during and after use of said device.

28. A device according to claim 27, wherein said device has locating means of insertion depth, first and second, disposed, respectively, on said hub and on said housing for locating a position of said housing relative to said hub longitudinally to said axis of said needle, said position corresponding to said determined insertion depth.

29. A device according to claim 28, wherein said first locating means of insertion depth comprises at least one circumferentially arranged positioning tooth and said second locating means of insertion depth comprises at least one circumferentially arranged aperture.

30. A device according to claim 27, wherein said device has information means of insertion depth disposed on at least one component part chosen from a group comprising said housing and said protecting shield.

* * * * *